US010351986B2

(12) United States Patent
Yoneda et al.

(10) Patent No.: US 10,351,986 B2
(45) Date of Patent: Jul. 16, 2019

(54) LAUNDRY WASHING MACHINE AND METHOD FOR DETECTING ATTACHED SUBSTANCE

(71) Applicant: Panasonic Intellectual Property Management Co., Ltd., Osaka (JP)

(72) Inventors: Aki Yoneda, Hyogo (JP); Naoyuki Harada, Osaka (JP); Tatsuo Itoh, Osaka (JP); Koichi Kusukame, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 104 days.

(21) Appl. No.: 14/941,148

(22) Filed: Nov. 13, 2015

(65) Prior Publication Data

US 2016/0160423 A1 Jun. 9, 2016

(30) Foreign Application Priority Data

Dec. 5, 2014 (JP) .................................. 2014-247014

(51) Int. Cl.
*D06F 39/00* (2006.01)
*D06F 33/02* (2006.01)
(Continued)

(52) U.S. Cl.
CPC ............ *D06F 39/004* (2013.01); *D06F 33/02* (2013.01); *D06F 39/02* (2013.01); *G01N 33/18* (2013.01);
(Continued)

(58) Field of Classification Search
CPC ........ D06F 39/004; D06F 33/02; D06F 39/02; D06F 39/08; D06F 37/30
See application file for complete search history.

(56) References Cited

U.S. PATENT DOCUMENTS 4,655,235 A * 4/1987 Scott, Jr. ................ A62B 99/00
134/113
5,603,233 A * 2/1997 Erickson ............. A47L 15/0021
68/12.02
(Continued)

FOREIGN PATENT DOCUMENTS

JP 54-071870 6/1979
JP 3-215293 A 9/1991
(Continued)

OTHER PUBLICATIONS

Machine translation of JP 05-154277 A, no date.*

*Primary Examiner* — Joseph L. Perrin
(74) *Attorney, Agent, or Firm* — Greenblum & Bernstein, P.L.C.

(57) ABSTRACT

A laundry washing machine includes a wash tub that allows laundry and water to be loaded therein, a holding unit that separates some of the water in the wash tub and holds the some of the water, where the water contains a substance that was attached to the laundry and that is dissolved therein, a detection unit that detects a predetermined substance contained in the some of the water held by the holding unit and outputs information indicating a result of detection, and a laundry detergent dispenser that dispenses a laundry detergent into the wash tub or instructs a user to add the laundry detergent to the wash tub after the some of the water is separated.

18 Claims, 17 Drawing Sheets

(51) Int. Cl.
  *D06F 39/02* (2006.01)
  *G08C 17/02* (2006.01)
  *G01N 33/18* (2006.01)
  *D06F 39/08* (2006.01)
  *D06F 37/30* (2006.01)
  *G06F 3/14* (2006.01)
(52) U.S. Cl.
  CPC .............. *G08C 17/02* (2013.01); *D06F 37/30* (2013.01); *D06F 39/08* (2013.01); *G06F 3/14* (2013.01)

(56) References Cited

U.S. PATENT DOCUMENTS

| | | | | |
|---|---|---|---|---|
| 2003/0213069 A1* | 11/2003 | Tortorici, Jr. | ......... | D06F 39/004 8/158 |
| 2010/0125364 A1* | 5/2010 | Ebrom | .................... | D06F 33/02 700/275 |
| 2011/0273714 A1* | 11/2011 | Pimputkar | .......... | A47L 15/4297 356/442 |
| 2012/0266388 A1* | 10/2012 | Pollett | ................... | D06F 39/004 8/137 |
| 2013/0061403 A1 | 3/2013 | Bringewatt et al. | | |
| 2013/0123589 A1 | 5/2013 | Moritani et al. | | |
| 2014/0053611 A1* | 2/2014 | Klos | ...................... | D06F 39/02 68/12.13 |
| 2015/0380451 A1* | 12/2015 | Kurokawa | ........ | H01L 27/14621 257/43 |

FOREIGN PATENT DOCUMENTS

| | | |
|---|---|---|
| JP | 05154277 A * | 6/1993 |
| JP | 05154278 A * | 6/1993 |
| JP | 5-200189 A | 8/1993 |
| JP | 2006-026037 A | 2/2006 |
| JP | 2006-343134 | 12/2006 |
| JP | 2010-148692 | 7/2010 |
| JP | 2013-523428 A | 6/2013 |
| WO | 2012/121260 | 9/2012 |

* cited by examiner

| DATE | CEDAR POLLEN ANTIGEN | CYPRESS POLLEN ANTIGEN |
|---|---|---|
| 9/1/2014 | A | B |
| 9/8/2014 | C | D |
| 9/15/2014 | E | F |

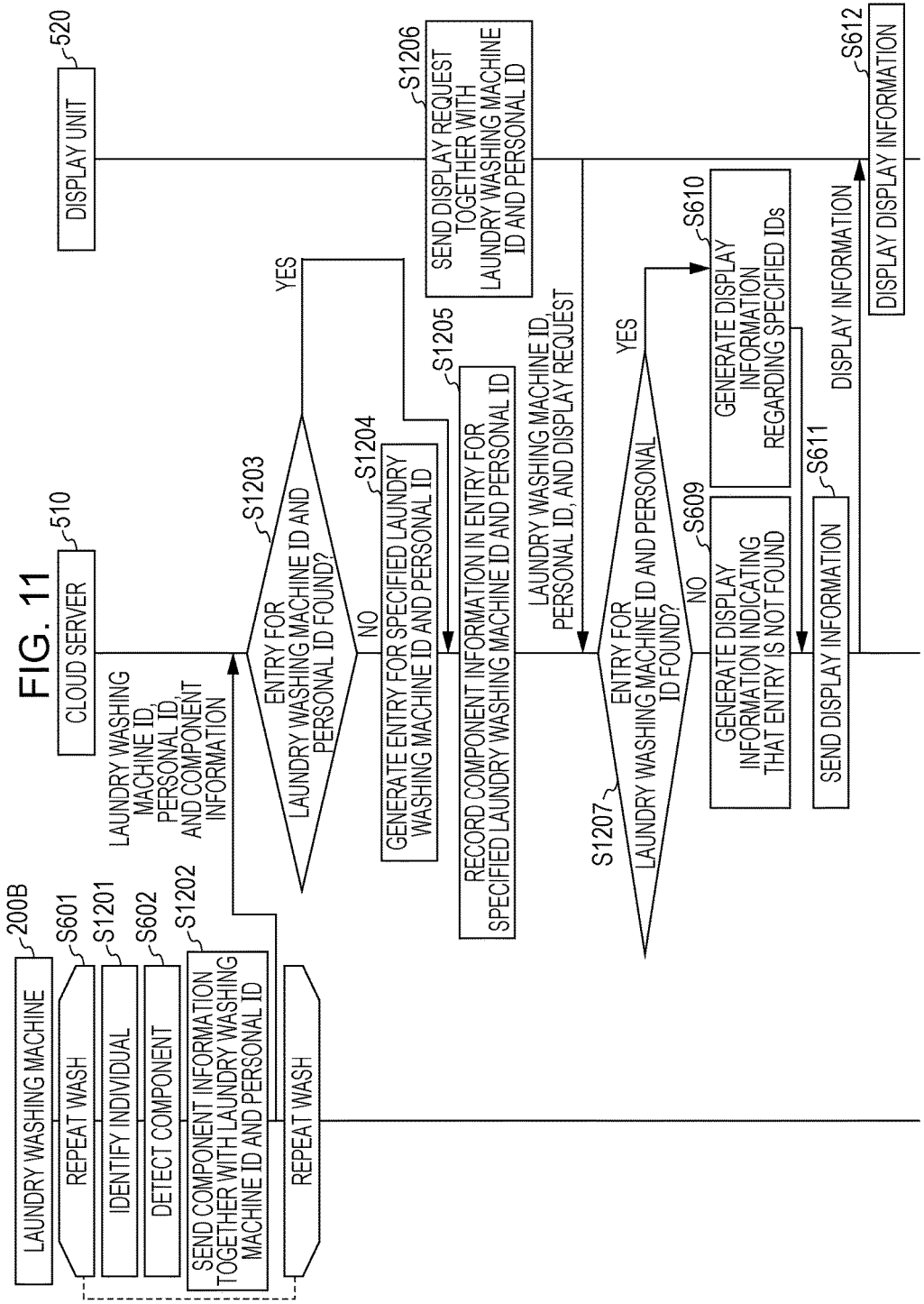

FIG. 12

| SUBSTANCE | LIKELY DISEASES |
|---|---|
| ACETONE | DIABETES, OBESITY, IMPROPER DIET |
| AMMONIA | DETERIORATION IN KIDNEY OR LIVER FUNCTION, ENTERAL ENVIRONMENT DETERIORATION, GOUT |
| NITRIC OXIDE | ASTHMA BRONCHIALE |
| HYDROGEN SULFIDE | GASTROINTESTINAL DISEASE |
| TRANS-2-NONENAL | SEVERE BODY ODOR OF OLD PEOPLE |
| 3-METHYL-3-SULFANYLHEXAN-1-OL | MENTAL STRESS (ORIGIN OF ARMPIT ODOR) |

FIG. 13

| PERSONAL ID | DATE | ACETONE | AMMONIA |
|---|---|---|---|
| DAD | 9/1/2014 | A | B |
| DAD | 9/8/2014 | C | D |
| DAD | 9/15/2014 | E | F |
| MOM | 9/1/2014 | G | H |
| MOM | 9/8/2014 | I | J |
| MOM | 9/15/2014 | K | L |
| JOHN | 9/1/2014 | M | N |
| JOHN | 9/8/2014 | O | P |
| JOHN | 9/15/2014 | Q | R |

LAUNDRY WASHING MACHINE AND METHOD FOR DETECTING ATTACHED SUBSTANCE

BACKGROUND

1. Technical Field

The present disclosure relates to a laundry washing machine and an attached substance detecting method.

2. Description of the Related Art

In recent years, the following technique has been increasingly used for daily personal healthcare. Users wear a wearable device on their body to acquire biological information, such as pulse and blood pressure and accumulate the acquired information in a server. However, the information regarding pulse or blood pressure is insufficient as detailed information used to detect a slight change in the physical condition caused by, for example, a furtive disease.

In addition, nowadays, a substance that is important to help assess the physical condition (e.g., gas or secretion which originates from the human body) can be relatively easily measured due to advances in semiconductor sensors.

Accordingly, the idea of measuring a substance which originates from the human body using a wearable device has been raised. For example, International Publication No. WO2012/121260 describes a technology of causing a user to wear a device, such as a headphone or an earphone, having a biological gas sensor disposed therein and detecting biological gas generated by the ear of the user. In addition, Japanese Unexamined Patent Application Publication No. 2010-148692 describes the configuration of a device for detecting biological gas generated by mainly the navel.

SUMMARY

In one general aspect, the techniques disclosed here feature a laundry washing machine including a wash tub that allows laundry and water to be loaded thereinto, a holder that separates some of the water in the wash tub and holds the some of the water, a detector that detects a predetermined substance contained in the some of the water held by the holding unit and outputs information indicating a result of detection, and a laundry detergent dispenser that dispenses a laundry detergent into the wash tub or instructs a user to add the laundry detergent to the wash tub after the some of the water is separated.

The laundry washing machine of the present disclosure can efficiently detect the substance which originates from the human body or the environment.

It should be noted that general or specific embodiments may be implemented as a system, a method, an integrated circuit, a computer program, a computer-readable recording medium, such as a compact disc read only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 11 is a sequence diagram of an attached substance detecting method according to the third exemplary embodiment;

FIG. 12 illustrates an example of a relationship between a substance that originates from the human body and a disease estimated from the substance;

FIG. 13 illustrates an example of the component information in the attached substance detecting method according to the third exemplary embodiment;

DETAILED DESCRIPTION

Underlying Knowledge Forming Basis of the Present Disclosure

The systems described in International Publication No. WO2012/121260 and Japanese Unexamined Patent Application Publication No. 2010-148692 detect biological gas which originates from the human body using a device worn by the human body and detect a change in the physical condition that could not be detected from the pulse or blood pressure. Thus, the systems can contribute to manage user's healthcare.

However, it is unpleasant for the user to spend a full day with any device worn. Due to the unpleasantness, this healthcare management method is not an efficient method. That is, in the systems described in International Publication No. WO2012/121260 and Japanese Unexamined Patent Application Publication No. 2010-148692, users need to wear a special device, such as a biological gas sensor, which is unpleasant for the users.

Accordingly, the present inventors conceived an idea of detecting the biological gas or secretion of the human body (hereinafter also referred to as a "predetermined substance") from clothing worn by the user instead of a device worn by the user.

In addition, the clothing is washed after being worn, in general. Accordingly, the present inventors conceived an idea of detecting the predetermined substance during washing. Thus, the result of detection of the predetermined substance contributes to manage user's healthcare and contributes to promote wearer's health.

A technique of sensing of the state of water solution in a wash tub is described in Japanese Unexamined Patent Application Publication No. 54-71870. Japanese Unexamined Patent Application Publication No. 54-71870 describes a technology that detects the dirt level of the water in the wash tub by measuring the transmittance of light and adjusts the amount of laundry detergent in accordance with the dirt level.

Figure 19:
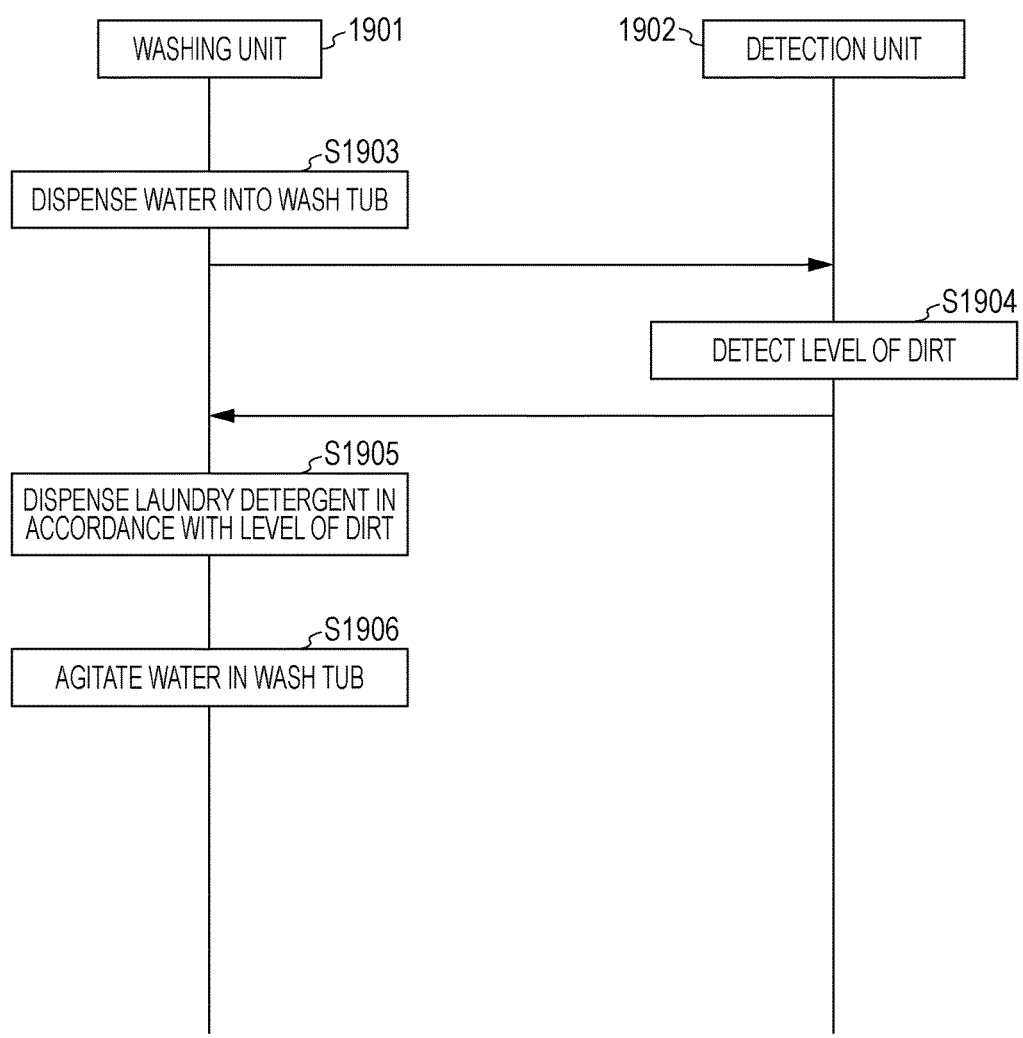
FIG. 19 is a sequence diagram illustrating the operation performed by an existing laundry washing machine.

FIG. 19 is a sequence diagram illustrating the operation performed by an existing laundry washing machine. More specifically, FIG. 19 is a sequence diagram illustrating the operation performed by the laundry washing machine described in Japanese Unexamined Patent Application Publication No. 54-71870.

When a washing cycle is started, a washing unit 1901 dispenses water into the wash tub (S1903). Thereafter, a detection unit 1902 detects the level of dirt in the water in the wash tub (S1904). Subsequently, the washing unit 1901 dispenses an amount of laundry detergent in accordance with the level of dirt (S1905). Wash is done by the wash tub having the laundry detergent dispensed thereinto (S1906).

In the above-described configuration described in Japanese Unexamined Patent Application Publication No. 54-71870, after the completion of detection of the level of dirt (S1904), the laundry detergent is dispensed, and the wash cycle is stated. That is, start of the wash cycle is delayed until completion of detection of the level of dirt. However, this delay of start of the wash is not a problem for detection described in Japanese Unexamined Patent Application Publication No. 54-71870, since the level of dirt in the water in the wash tub is measured using the light transmittance and, thus, it takes only a few seconds to measure the level of dirt.

In contrast, the present disclosure aims to detect a tiny amount of a substance (e.g., the above-described secretion) used for estimating the physical condition and the disease tendency. To detect a tiny amount of a substance, a technique called "liquid chromatography" can be used. The liquid chromatography technique uses the time difference between the times at which substances that have passed through a column and are discharged from the column. The time difference is caused by the different levels of absorption of a substance disposed in the column against the substances to be measured. That is, to perform accurate analysis using liquid chromatography, a large time difference is needed. Thus, in principle, a certain length of time is required for detection. Typically, several minutes to several tens of minutes are required. A delay time of several minutes to several tens of minutes before start of the wash cycle causes a serious problem.

In addition, in a technique for detecting a pollen antigen described in Japanese Unexamined Patent Application Publication No. 2006-343134, solution is vibrated by ultrasonic waves for about five minutes in order to extract the contents of pollen. That is, more than five minutes are required for measurement. Such delay time before start of the washing cycle causes a serious problem.

The present disclosure provides a laundry washing machine that efficiently detects a substance which originates from the human body or the environment.

According to an aspect of the present disclosure, a laundry washing machine includes a wash tub that allows laundry and water to be loaded thereinto, a holding unit that separates some of the water in the wash tub and holds the some of the water, a detection unit that detects a predetermined substance contained in the some of the water held by the holding unit and outputs information indicating a result of detection, and a laundry detergent dispenser that dispenses a laundry detergent into the wash tub or instructs a user to add the laundry detergent to the wash tub after the some of the water is separated.

According to such a configuration, the laundry washing machine detects a predetermined substance in the water that is separated from the water in the wash tub and that contains a substance dissolved therein. To detect the predetermined substance, a detection technique, such as liquid chromatography, is employed. The detection technique requires a certain length of time to detect the predetermined substance. If the water is not separated from the wash tub, a laundry detergent cannot be dispensed for washing until the result of detection of the predetermined substance is obtained. Since as described above, the laundry washing machine according to the aspect of the present disclosure separates the water containing a substance to be detected from the wash tub, the laundry detergent can be dispensed into the wash tub for washing without waiting for the result of detection being obtained. Thus, the laundry washing machine can efficiently detect the predetermined substance that originates from the human body or the environment.

That is, the laundry washing machine according to the aspect of the present disclosure temporarily stores the water solution located in the wash tub before the laundry detergent is dispensed into the wash tub and detects the predetermined substance in the stored water solution. In addition, the laundry detergent is dispensed into the wash tub during detection, and a wash is started. In this manner, wash can be done during detection that requires much time. Thus, an excellent effect that eliminates the need for a waiting time before a wash is started can be provided.

In addition, the laundry washing machine can detect a substance that originates from the human body or a substance in the environment that has an adverse effect on the human body even when the user does not wear any special device in daily life as usual. Thus, the laundry washing machine can contribute to the health management of the user.

For example, the wash tub washes the laundry using the laundry detergent after the laundry detergent is dispensed by the laundry detergent dispenser or the laundry detergent is added by the user on the basis of the instruction from the laundry detergent dispenser, and the detection unit performs the detection while the wash tub is in a wash cycle.

In this manner, the laundry washing machine detects the predetermined substance attached to the laundry during washing time of the laundry. In this manner, the laundry washing machine can detect the predetermined substance concurrently with the washing of the laundry. Thus, a period of time dedicated to detection of the predetermined substance is not needed. As a result, the laundry washing machine can efficiently detect the substance which originates from the human body or the environment.

For example, the wash tub agitates the loaded laundry and water, and the holding unit separates the some of the water in the wash tub after the wash tub agitates the laundry and the water and before the laundry detergent dispenser dispenses the laundry detergent or instructs the user to add the laundry detergent.

In this manner, the laundry washing machine actively dissolves the substance that was attached to the laundry in the water and separates some of the water having the substance dissolved therein. Thereafter, the laundry washing machine detects the predetermined substance in the separated water. Thus, the laundry washing machine can more accurately detect the substance which originates from the human body or the environment.

For example, the laundry washing machine further includes a control unit that controls the wash tub, the laundry detergent dispenser, the holding unit, and the detection unit. The control unit causes the wash tub to agitate the laundry and the water before the holding unit separates the some of the water in the wash tub and causes the holding unit to separate the some of the water in the wash tub after the wash tub agitates the laundry and the water. After the holding unit completes separating the some of the water in the wash tub, the control unit causes the wash tub to start agitating the laundry and the water again and instructs the laundry detergent dispenser to dispense the laundry detergent into the wash tub or instruct the laundry detergent dispenser to instruct the user to add the laundry detergent to the wash tub.

In this manner, by controlling, in particular, the wash tub, the laundry detergent dispenser, the holding unit, and the detection unit, the laundry washing machine can provide effects that are the same as the above-described effects.

For example, after the detection unit performs the detection, the control unit controls a wash course of the wash done by the wash tub on the basis of the result of detection.

In this manner, the laundry washing machine changes the setting for wash to more suitable setting on the basis of the result of detection of the predetermined substance. Thus, the laundry washing machine can more thoroughly wash away the predetermined substance attached to the laundry.

For example, the wash course is defined as setting at least one of an amount of the laundry detergent dispensed by the laundry detergent dispenser, a time length of the wash cycle of the wash tub, and a time length of a rinse cycle of the wash tub and washing the laundry using the wash tub.

In this manner, the laundry washing machine changes the setting for wash to more suitable and particular setting on the basis of the result of detection of the predetermined substance. Thus, the laundry washing machine can more thoroughly wash away the predetermined substance attached to the laundry.

For example, the laundry washing machine further includes an information aggregation unit that aggregates information on the basis of the result of detection output from the detection unit and a display unit that displays the aggregated information. After the detection unit performs the detection, the control unit causes the information aggregation unit to aggregate the information and causes the display unit to display the information aggregated by the information aggregation unit.

For example, the laundry washing machine further includes a transceiver unit that communicates information with an external apparatus that aggregates information on the basis of the result of detection and a display unit that displays information received from the external apparatus. After the detection unit performs the detection, the control unit causes the transceiver unit to send, to the external apparatus, the result of detection and appliance identification information for identifying the laundry washing machine. If the transceiver unit receives information aggregated on the basis of the result of detection from the external apparatus, the control unit causes the display unit to display, on the display unit, the received aggregated information.

For example, the laundry washing machine further includes a transceiver unit that communicates information with an external apparatus that aggregates information on the basis of the result of detection and an individual identifying unit that identifies personal information regarding the laundry loaded into the wash tub. After the detection unit performs the detection, the control unit causes the transceiver unit to send, to the external apparatus, the personal information, the result of detection, and appliance identification information for identifying the laundry washing machine, and the control unit causes the external apparatus to send, to an external display terminal associated with the personal information, information aggregated on the basis of the result of detection.

In this manner, the laundry washing machine can appropriately display, on the display unit, the result of detection performed by the detection unit and present the result of detection to the user.

For example, the detection unit performs the detection every time the wash is done and outputs a plurality of results of the detection. The laundry washing machine further includes an information accumulating unit that accumulates, in a writable recording medium, the result of detection in association with a time at which the result of detection is output every time the detection unit outputs the information and a display unit that displays each of the results of detection accumulated in the recording medium in association with the time at which the result of detection was output.

In this manner, the laundry washing machine displays the temporal variation of the result of detection obtained through the plurality of washes. By viewing the information displayed by the laundry washing machine, the user can find out a temporal decrease or increase in the amount of the predetermined substance. In this manner, the user can take an action according to the temporal variation of the amount of the predetermined substance.

For example, the detection unit detects, as the predetermined substance, a substance that is floating in the air and that is attached to the laundry.

In this manner, the laundry washing machine particularly detects the substance floating in the air as the predetermined substance. The user can be aware of the result of detection of the substance floating in the air. Thus, the user can take an action that protects themselves, such as wearing or not wearing a mask or a cap, depending on the amount of the predetermined substance.

For example, the detection unit detects, as the predetermined substance, an antigen present in pollen.

In this manner, the laundry washing machine particularly detects the antigen present in a pollen as the predetermined substance. The user can be aware of the result of detection of the antigen present in a pollen. Thus, the user can take an action that protects themselves, such as wearing a mask or a cap, depending on the amount of the antigen present in the pollen.

For example, the detection unit detects, as the predetermined substance, a substance that originates from the human body which wore the laundry and that is attached to the laundry.

In this manner, the laundry washing machine particularly detects the substance which originates from the human body as the predetermined substance. The user can be aware of the result of detection of the substance which originates from the human body. Thus, the user can control health management, such as starting exercising or food control, depending on an increase or a decrease in the amount of the substance which originates from the human body.

For example, the laundry washing machine further includes an individual identifying unit that identifies a person who wore the laundry. The information accumulating unit further accumulates, in the recording medium, the result of detection in association with a personal ID indicating the person identified by the individual identifying unit. The display unit receives a specified personal ID representing a personal ID specified by the user, reads out, from the recording medium, the result of detection associated with the specified personal ID received, and displays each of the readout results of detection in association with the time at which the result of detection was output.

In this manner, the laundry washing machine displays the temporal variation of the result of detection of the predetermined substance for a specified person. Thus, the user can find out the information regarding the specified person in more detail. Note that the specified person may be the user themselves or a person other than the user.

For example, the display unit further displays information in accordance with a variation of a physical condition of the person, and the variation of the physical condition is estimated on the basis of a temporal variation of the amount of the substance detected by the detection unit.

In this manner, the laundry washing machine can present a change in the physical condition of the specified person on the basis of the temporal variation of the result of detection for the person and display alert information if, for example, the physical condition is getting worse. The user can take an action plan to improve their health, such as a food plan and an exercise plan.

For example, the detection unit performs the detection using liquid chromatography.

In this manner, the laundry washing machine detects the predetermined substance using, in particular, liquid chromatography. Thus, the laundry washing machine can more accurately detect the predetermined substance.

For example, the laundry washing machine further includes a window disposed in part of a housing of the laundry washing machine. A component that constitutes the detection unit and that requires replacement is replaced with a new one through the window.

In this manner, the laundry washing machine allows a part used for detecting the predetermined substance to be replaced through the window. The user can replace a component with a new one in a simpler way without disassembling the laundry washing machine.

For example, the holding unit includes a tank that holds the some of the water, a water channel that draws the some of the water in the wash tub into the tank, and a valve disposed in the water channel. The some of the water in the wash tub is held in the tank by opening the valve, and the some of the water is separated from the wash tub by closing the valve.

In this manner, the laundry washing machine can dispense the water in the wash tub into the tank and, thereafter, separate the water in the tank from the water in the wash tub using, in particular, a valve. Thus, the laundry washing machine can more reliably separate, from the water in the wash tub, some of the water from which the predetermined substance is to be detected and, thereafter, detect the predetermined substance.

According to another aspect of the present disclosure, an attached substance detecting method for use in an attached substance detection system is provided. The attached substance detection system includes a laundry washing machine having a wash tub therein, and the wash tub allows laundry and water to be loaded thereinto. The method include separating some of the water in the wash tub and holding the some of the water, detecting a predetermined substance contained in the held some of the water and outputting information indicating the result of detection, and dispensing a laundry detergent into the wash tub or instructing a user to add the laundry detergent to the wash tub after the some of the water is separated.

In this manner, the effect the same as that of the laundry washing machine can be provided.

For example, in detecting a predetermined substance contained in the held some of the water and outputting information indicating the result of detection, every time the detection is performed, the result of the detection is output. The method further includes accumulating, in a writable recording medium, the result of detection in association with a time at which the result of detection is output every time the result of detection is output and displaying each of the accumulated results of detection in association with the time at which the result of detection was output.

In this manner, the effect the same as that of the laundry washing machine can be provided.

For example, the attached substance detecting method further includes identifying the human body that wore the laundry on a person-to-person basis. In accumulating the result of detection in a writable recording medium, the result of detection is accumulated in association with a personal ID indicating the identified person. In displaying each of the accumulated results of detection, a specified personal ID representing a personal ID specified by a user is received, the result of detection associated with the received specified personal ID is read out from the recording medium, and each of the readout results of detection is displayed in association with the time at which the result of detection was output.

In this manner, the effect the same as that of the laundry washing machine can be provided.

For example, in displaying each of the accumulated results of detection, information in accordance with a variation of a physical condition of the person is further displayed, where the variation of the physical condition is estimated on the basis of a temporal variation of the amount of the detected substance.

In this manner, the effect the same as that of the laundry washing machine can be provided.

It should be noted that these general or specific aspects may be implemented as a system, a method, an integrated circuit, a computer program, a storage medium, such as a computer-readable CD-ROM, or any selective combination thereof.

Exemplary embodiments are described in detail below with reference to the accompanying drawings.

Note that each of the embodiments below describes a general or specific example. A value, a shape, a material, a constituent element, the positions and the connection form of the constituent elements, steps, and the sequence of steps used in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

First Exemplary Embodiment

Apparatus for Detecting Substance Attached to Laundry

Figure 1:
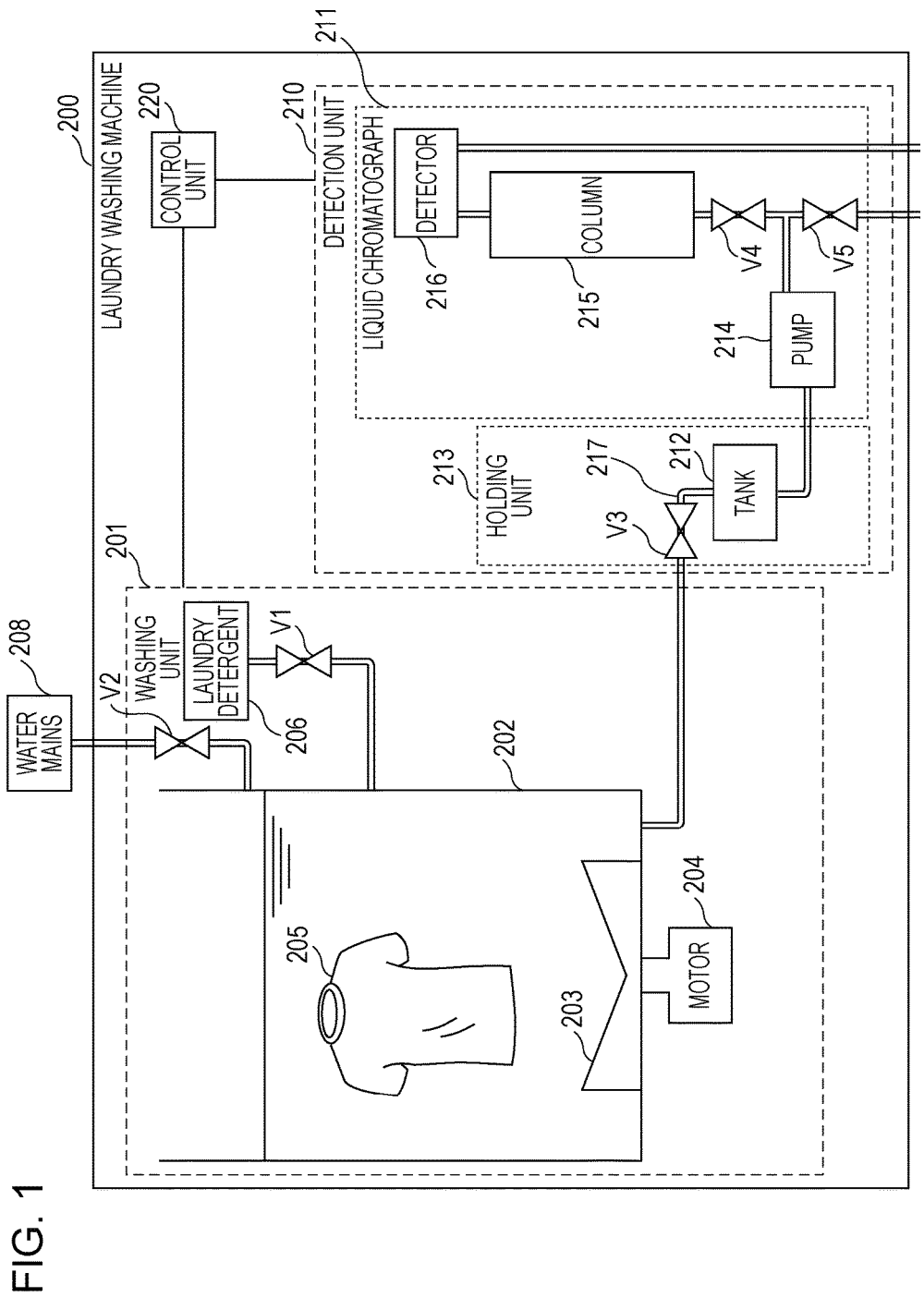
FIG. 1 is a block diagram of the configuration of a laundry washing machine according to a first exemplary embodiment.

FIG. 1 is a block diagram of the configuration of a laundry washing machine 200 according to a first exemplary embodiment. The laundry washing machine 200 washes laundry.

As illustrated in FIG. 1, the laundry washing machine 200 includes a washing unit 201, a detection unit 210, and a control unit 220.

The washing unit 201 washes laundry. The washing unit 201 includes a wash tub 202. The wash tub 202 holds the water dispensed from the water mains 208. That is, water delivered from the water mains 208 is dispensed into the wash tub 202.

In addition, laundry 205 is put into the wash tub 202 by, for example, a user. By agitating the put laundry 205 and the water, the wash tub 202 dissolves a substance attached to the laundry 205 with the water. For example, the bottom surface of the wash tub 202 has a pulsator 203 at the center thereof. The pulsator 203 has a motor 204 attached thereto. For example, the rotation shaft (not illustrated) of the motor 204 is attached to the center portion of the pulsator 203. Rotation of the motor 204 rotates the pulsator 203. In this manner, the wash tub 202 agitates the put laundry 205 and the water.

When a laundry detergent 206 is further dispensed into the wash tub 202, a processing unit of the washing unit 201 drives the motor 204 again. The pulsator 203 rotated by the motor 204 agitates the water containing the laundry detergent 206 and the laundry 205. In this manner, the laundry 205 is cleaned. That is, the laundry 205 is washed.

Note that the washing unit 201 may include, for example, a processing unit (not illustrated). In such a case, upon receiving a signal from the control unit 220, the processing unit of the washing unit 201 controls the operation to open and close valves V1 and V2 and controls the wash tub 202. An example of control of the wash tub 202 is control of the rotation of the pulsator 203 by controlling driving of the motor 204. In addition, the processing unit of the washing unit 201 receives a signal from the control unit 220 and sends a signal to the control unit 220.

The processing unit of the washing unit 201 includes, for example, a processing circuit (not illustrated), such as a processor, and a memory (not illustrated). The memory stores a program that causes the processing circuit to function as the processing unit of the washing unit 201. When the processing circuit executes the program, the processing unit of the washing unit 201 functions. Alternatively, an integrated circuit having a function realized by execution of the above-described program may be used as the processing unit of the washing unit 201.

The valve V1 is disposed in, for example, a channel through which the laundry detergent 206 is dispensed into the wash tub 202. If the valve V1 opens, the laundry detergent 206 is supplied into the wash tub 202. In contrast, if the valve V1 is closed, supply of the laundry detergent 206 to the wash tub 202 is stopped. For example, upon receiving an electrical signal for opening the valve V1, the valve V1 operates to open. In addition, for example, upon receiving an electrical signal for closing the valve V1, the valve V1 operates to close.

The valve V2 is disposed in, for example, a water channel through which tap water supplied from the water mains 208 is dispensed into the wash tub 202. If the valve V2 opens, tap water is supplied from the water mains 208 into the wash tub 202 via the water channel. In contrast, if the valve V2 is closed, supply of the tap water from the water mains 208 to the wash tub 202 is stopped. For example, upon receiving an electrical signal for opening the valve V2, the valve V2 operates to open. In addition, for example, upon receiving an electrical signal for closing the valve V2, the valve V2 operates to close. The timing at which water is dispensed from the water mains 208 to the wash tub 202 and the amount of water are controlled by electrically opening and closing the close valve V2. The timing at which the laundry detergent 206 is dispensed and the amount of the laundry detergent 206 are controlled by electrically opening and closing the close valve V1. For example, the valve V1 corresponds to a laundry detergent dispenser.

Note that the above-described configuration of the washing unit 201 is only an example. Another configuration of the washing unit 201 can be employed.

The term "water" as used herein is not to be understood as being strictly limited to pure water. Instead, water is intended to mean both water solution containing a relatively small amount of impurity and liquid used for laundry. In addition, the term "laundry" refers to clothing worn on the human body and a towel and a handkerchief that allow a substance which originates from the human body to adhere thereto.

The detection unit 210 detects the predetermined substance attached on the laundry 205. The detection unit 210 includes, for example, a holding unit 213 and a liquid chromatograph 211. The detection unit 210 and the wash tub 202 are connected to each other using, for example, a water channel. In addition, the detection unit 210 may further include a processing unit (not illustrated). In such a case, upon receiving a signal from the control unit 220, the processing unit of the detection unit 210 performs, for example, control of the holding unit 213, control of driving of a pump 214, open/close control of valves V4 and V5, and control of outputting the result of detection of a detector 216 to the control unit 220. An example of the control of the holding unit 213 is control of the operation to hold, in a tank 212, the water dispensed from the wash tub 202 by controlling the open/close operation performed by the valve V3. In addition, the processing unit of the detection unit 210 receives a signal from the control unit 220 and sends a signal to the control unit 220. The processing unit of the detection unit 210 includes, for example, a processing circuit (not illustrated), such as a processor, and a memory (not illustrated). The memory stores a program that causes the processing circuit to function as the processing unit of the detection unit 210. By executing the program, the processing unit of the detection unit 210 functions. Alternatively, an integrated circuit having a function realized by execution of the above-described program may be used as the processing unit of the detection unit 210.

The holding unit 213 separates some of the water that is in the wash tub 202 and that contains dissolved substance attached to the laundry 205 and holds the separated water. The holding unit 213 includes the tank 212, a valve V3, and a water channel 217.

The tank 212 temporarily holds the water retrieved from the wash tub 202.

The water channel 217 draws the water from the wash tub 202 into the tank 212 so as to fill the tank 212 with the water. The water channel 217 extends from, for example, the bottom portion of the wash tub 202 and is connected to the tank 212.

The valve V3 is disposed in the water channel 217 that connects the wash tub 202 to the holding unit 213. By opening the valve V3, the water in the wash tub 202 is fed to the tank 212. In addition, by closing the valve V3, feeding of the water to the tank 212 is stopped. For example, upon receiving an electrical signal for opening the valve V3, the valve V3 operates to open. Upon receiving an electrical signal for closing the valve V3, the valve V3 operates to close. If the valve V3 closes and stops the flow of the water in the water channel 217, the water of the wash tub 202 (some of the water) is separated from other water in the wash tub 202. The control of the open/close operation of the valve V3 is performed on the basis of, for example, an electrical signal sent from the control unit 220.

The detection unit 210 detects a predetermined substance contained in the water stored in the holding unit 213 and outputs information regarding the result of detection. The detection unit 210 includes the liquid chromatograph 211, the pump 214, a column 215, the detector 216, and the valves V4 and V5.

The liquid chromatograph 211 detects the components of the water stored in the tank 212 using liquid chromatography. Note that the liquid chromatography is an example of a component detection technique, and another component detection technique may be employed. For example, the pollen antigen detection technique described in Japanese Unexamined Patent Application Publication No. 2006-343134 can be employed.

The pump 214 uniformly delivers the water stored in the tank 212 to the column 215.

The column 215 isolates each of the substances by creating the difference in emission time using the difference in absorbability among substances.

The detector 216 detects the substance isolated by the column 215.

Each of the valves V4 and V5 is used to control whether the water in the tank 212 is delivered to the column 215 or is output to the outside of the laundry washing machine 200. The valve V4 is disposed in the water channel that connects the pump 214 to the column 215. If the valve V4 is open and the pump 214 operates, the water in the tank 212 is fed to the column 215. In addition, by closing the valve V4, feeding of the water to from the tank 212 to the column 215 is stopped. For example, upon receiving an electrical signal for opening the valve V4, the valve V4 operates to open. Upon receiving an electrical signal for closing the valve V4, the valve V4 operates to close. The valve V5 is disposed in a water channel for draining the water stored in the tank 212 to the outside of the laundry washing machine 200. One end of the water channel for draining the water stored in the tank 212 to the outside is connected to the pump 214. If the valve V5 is open and the pump 214 operates, the water in the tank 212 is drained to the outside of the laundry washing machine 200. In addition, by closing the valve V5, draining of the water stored in the tank 212 to the outside of the laundry washing machine 200 is stopped. For example, upon receiving an electrical signal for opening the valve V5, the valve V5 operates to open. Upon receiving an electrical signal for closing the valve V5, the valve V5 operates to close. Each of the valves V4 and V5 is electrically controlled by the control unit 220. That is, if the valve V4 is open and the valve V5 is closed, the water in the tank 212 is delivered to the column 215. In contrast, if the valve V4 is closed and the valve V5 is open, the water in the tank 212 is drained to the outside of the laundry washing machine 200.

The control unit 220 is a processing unit that controls each of the constituent elements of the laundry washing machine 200. More specifically, the control unit 220 controls the wash tub 202 via the processing units included in the washing unit 201 and the detection unit 210, controls the holding unit 213, controls the laundry detergent dispenser, controls the open/close operation of each of the valves V1 and V5, and controls driving of the pump 214. Note that the processing units included in the washing unit 201 and the detection unit 210 may be included in the control unit 220. In such a case, for example, the control unit 220 can directly send an instruction to the constituent elements of the laundry washing machine 200, and the processes performed by the constituent elements described in the exemplary embodiments can be performed by the constituent elements in accordance with the instructions. The control performed by the control unit 220 and the timing at which the control is performed are described in detail below.

The control unit 220 may include, for example, a processor and a memory (neither is illustrated). For example, the memory may store a program that causes the control unit 220 to function. For example, when the processer reads out the program stored in the memory and executes the program, the control unit 220 functions. Alternatively, an integrated circuit that has the function of the control unit 220 may be employed.

Instead of dispensing the laundry detergent 206 into the wash tub 202 by controlling the valve V1, the control unit 220 may instruct the user to add the laundry detergent 206 into the wash tub 202. In such a case, the control unit 220 corresponds to the laundry detergent dispenser.

Method for Detecting Substance Attached to Laundry

A particular operation performed by the apparatus for detecting a substance attached to laundry with the above-described configuration according to the first exemplary embodiment (a method for detecting a substance attached to laundry) is described below with reference to a sequence diagram illustrated in FIG. 2.

Figure 2:
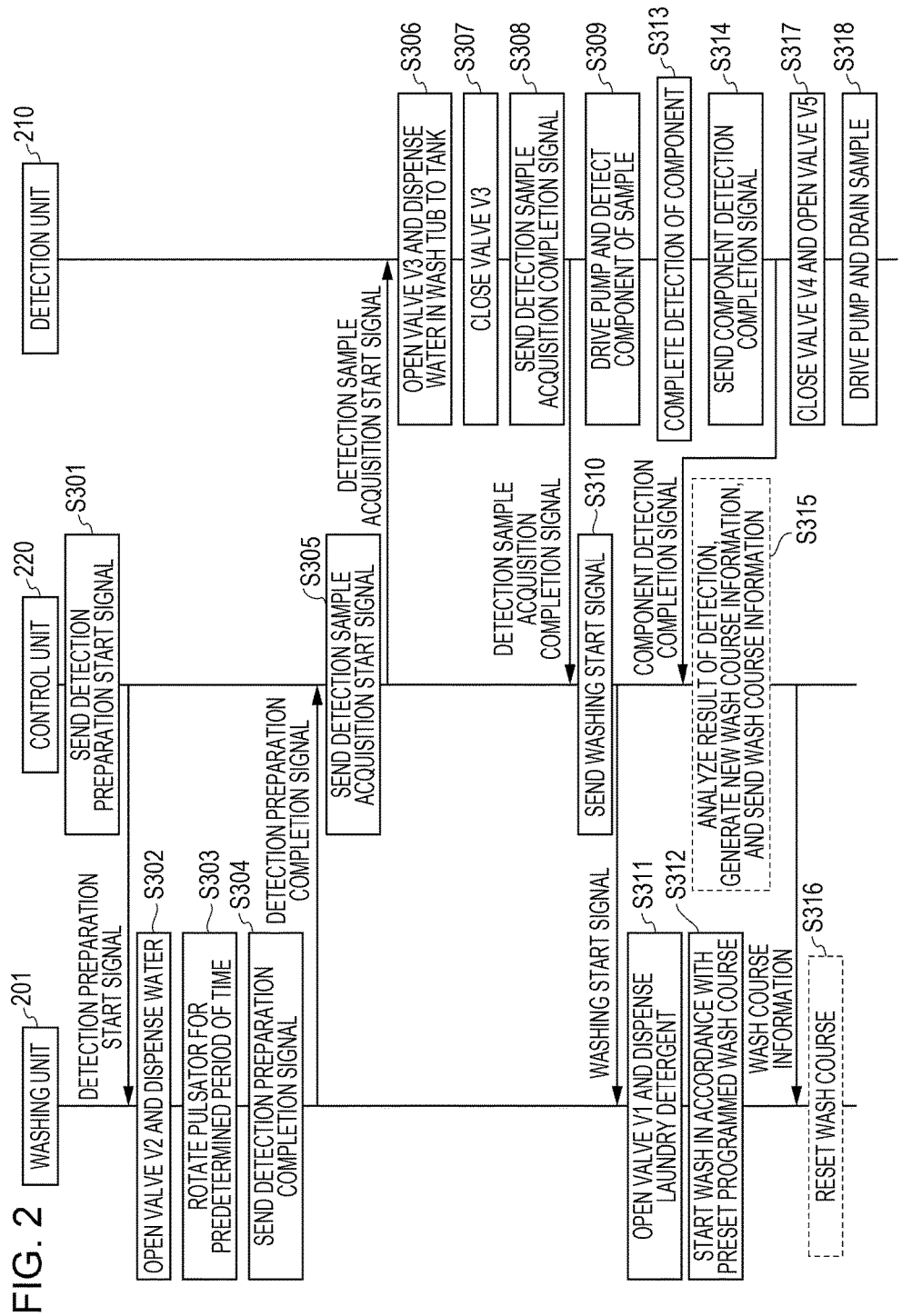
FIG. 2 is a sequence diagram illustrating an attached substance detecting method according to the first exemplary embodiment.

FIG. 2 is a sequence diagram illustrating the method for detecting a substance attached to laundry according to the first exemplary embodiment.

A user places the laundry 205 in the wash tub 202 and performs an operation to cause the laundry washing machine 200 to start its operation. At that time, any type of operation may be employed. For example, the operation is performed by the user pressing a start button provided on the laundry washing machine 200.

In step S301, the control unit 220 sends a detection preparation start signal to the washing unit 201 on the basis of the above-described operation. The detection preparation start signal is, for example, an electrical signal including an instruction for causing the washing unit 201 to perform a preparation for detecting a component.

In step S302, the processing unit of the washing unit 201 receives the detection preparation start signal. The washing unit 201 sends a signal for opening the valve V2 to the valve V2. Thus, upon receiving the signal, the valve V2 operates to open. After the valve V2 is open, water is dispensed from the water mains 208 into the wash tub 202. Alternatively, for example, the washing unit 201 may be configured so as to, if a certain amount of water is dispensed from the water mains 208 to the wash tub 202, send a signal for closing the valve V2 and close the valve V2.

In step S303, the processing unit of the washing unit 201 drives the motor 204 to rotate the pulsator 203 for a predetermined period of time. In this manner, the substance attached to the laundry is easily separated from the laundry so that the substance is dissolved in the water. Note that examples of the substance attached to the laundry include a substance attached to the laundry after being expelled from (secreted or created by) the human body that worn the laundry and a substance attached to the laundry after existing in the surrounding environment (e.g., floating in the air). The substance may be a substance composed by a living body, such as the human body, an artificially composed substance, or a substance that is found in nature, such as dirt or dust. Alternatively, the substance may be a pollen and, more specifically, a pollen antigen. Note that the term "dissolving a substance in water" means turning of water into mixed liquid containing the substance by mixing the substance and the water, turning of water into water solution by chemically coupling the substance with a water molecule, or causing the water to contain the substance.

In step S304, the processing unit of the washing unit 201 rotates the pulsator 203 for a predetermined period of time and, subsequently, sends a detection preparation completion signal to the control unit 220. The detection preparation completion signal is, for example, an electrical signal indicating that the pulsator 203 has been rotated for the predetermined period of time. At that time, the processing unit of the washing unit 201 may stop the rotation of the pulsator 203 by temporarily stopping driving of the motor 204.

In step S305, upon receiving the detection preparation completion signal, the control unit 220 sends a detection sample acquisition start signal to the processing unit of the detection unit 210. The detection sample acquisition start signal is, for example, an electrical signal including an instruction for causing the detection unit 210 to hold, in the holding unit 213 (more specifically, the tank 212), some of the water stored in the wash tub 202.

In step S306, upon receiving the detection sample acquisition start signal, the processing unit of the detection unit 210 sends a signal for opening the valve V3 to the valve V3. Upon receiving the signal for opening the valve V3, the valve V3 operates to open. In this manner, the water is dispensed from the wash tub 202 into the tank 212.

In step S307, after a predetermined amount of the water solution is stored in the tank 212, the processing unit of the detection unit 210 sends a signal for closing the valve V3 to the valve V3. Upon receiving the signal for closing the valve V3, the valve V3 operates to close. In this manner, the water channel between the wash tub 202 and the detection unit 210 is blocked and, thus, the water is not dispensed from the wash tub 202 into the tank 212.

In step S308, after the valve V3 is closed, the processing unit of the detection unit 210 sends a detection sample acquisition completion signal to the control unit 220. The detection sample acquisition completion signal is, for example, an electrical signal indicating that the operation to hold, in the holding unit 213 (more specifically, the tank 212), the water stored in the wash tub 202 is completed.

The detection unit 210 starts detecting a component asynchronously without waiting for any external signal. That is, the processing unit of the detection unit 210 sends a signal for opening the valve V4 to the valve V4 and sends a signal for closing the valve V5 to the valve V5. Upon receiving the signal for opening the valve V4, the valve V4 operates to open. Upon receiving the signal for closing the valve V5, the valve V5 operates to close. The processing unit of the detection unit 210 drives the pump 214 to deliver the water solution in the tank 212 to the column 215. The column 215 isolates the substance by creating the difference in emission time using the difference in absorbability among substances and supplies the isolated substance to the detector 216. The detector 216 detects the component of the substance supplied from the column 215 (S309). In this manner, the predetermined substance contained in the water solution held by the tank 212 is detected by the detector 216. Note that according to the present exemplary embodiment, the predetermined substance detected by the detector 216 is, for example, a substance that was attached to the laundry and that is dissolved in the water dispensed into the wash tub 202 or is mixed with the water.

In step S310, upon receiving the detection sample acquisition completion signal, the control unit 220 sends a washing start signal to the processing unit of the washing unit 201. The washing start signal is, for example, an electrical signal including an instruction for causing the washing unit 201 to start a wash.

In step S311, upon receiving the washing start signal, the processing unit of the washing unit 201 sends a signal for opening the valve V1 to the valve V1. Upon receiving the signal for opening the valve V1, the valve V1 operates to open. In this manner, the laundry detergent 206 is dispensed into the wash tub 202 so as to be mixed with the water solution in the wash tub 202. Since at that time, the valve V3 is closed, the water solution mixed with the laundry detergent 206 is not dispensed into the tank 212. Accordingly, the water solution mixed with the laundry detergent 206 has no impact on detection of a component. After the laundry detergent 206 is dispensed into the wash tub 202, the processing unit of the washing unit 201 sends a signal for closing the valve V1 to the valve V1. Upon receiving the signal for closing the valve V1, the valve V1 operates to close.

Note that in step S311, instead of dispensing the laundry detergent 206, the control unit 220 may instruct the user to add the laundry detergent 206 into the wash tub 202. This is effective when the valve V1 is not a valve that is controlled electrically. The instruction given by the control unit 220 to the user for adding the laundry detergent 206 into the wash tub 202 may be a message that is displayed on a display panel (not illustrated) of the laundry washing machine 200 and that instructs addition of the laundry detergent or a voice signal that is output from a speaker (not illustrated) of the laundry washing machine 200 and that instructs addition of the laundry detergent.

In step S312, the processing unit of the washing unit 201 starts washing in accordance with a preset programmed wash course. As used herein, the term "settings of a wash course" refers to settings of the time period or the number of wash cycles, rinse cycles, and spin cycles. At that time, for a preset wash course, the length of time for a wash cycle is set by the detection unit 210 so as to be longer than the length of time required for detecting the predetermined substance contained in the water solution stored in the wash tub 202.

In step S313, after a predetermined period of time has elapsed since start of detection of a component, the detection of a component of the substance contained in the water solution by the detection unit 210 is completed during washing. As described above, a component may be detected during the washing started in step S312. In this manner, the laundry washing machine 200 does not need a period of time used for only detection of the predetermined substance. Thus, the predetermined substance can be efficiently detected.

In step S314, the processing unit of the detection unit 210 sends a component detection completion signal to the control unit 220. The component detection completion signal includes, for example, information indicating that detection of the component of the substance performed by the detection unit 210 has been completed and information regarding the result of the component detection.

In step S315, upon receiving the component detection completion signal, the control unit 220 analyzes the result of detection of the substance using the detection unit 210. Thereafter, the control unit 220 generates a signal including new wash course information and sends the signal to the washing unit 201. As used herein, the term "wash course information" refers to information including at least one of the amount of the laundry detergent 206 to be dispensed, the wash cycle time of the wash tub 202, and the rinse cycle time of the wash tub 202. The wash course information determines the operation related to a wash done by the laundry washing machine 200.

The case in which trans-2-nonenal, for example, is detected in step S309 is discussed below. Trans-2-nonenal is a substance responsible for body odor of old people and has a particular odor. If the control unit 220 detects, from the result of detection of the substance performed by the detection unit 210, that the amount of detected trans-2-nonenal is greater than a predetermined amount, the control unit 220 generates wash course information regarding a new wash course that for example, additionally dispenses the laundry detergent 206, extends the wash time, or dispenses a fabric softener containing a deodorant in addition to the laundry detergent 206 in order to remove the body odor. Note that for example, a new wash course is a wash course different from the preset wash course.

In step S316, upon receiving the wash course information, the washing unit 201 changes the settings to the new wash course indicated by the received wash course information. Thereafter, the washing unit 201 performs at least one of the following processes in accordance with the reset wash course: a process to additionally dispense the laundry detergent 206, a process to change the wash cycle time of the wash tub 202, and a process to change a rinse cycle time of the wash tub 202. In this manner, the wash tub 202 does a wash that is optimum in accordance with the substance attached to the laundry 205 to be placed therein.

In step S317, the processing unit of the detection unit 210 sends a signal for closing the valve V4 to the valve V4 and sends a signal for opening the valve V5 to the valve V5. Upon receiving the signal for closing the valve V4, the valve V4 operates to close. Upon receiving the signal for opening the valve V5, the valve V5 operates to open.

In step S318, the processing unit of the detection unit 210 drives the pump 214 to drain the water solution stored in the tank 212 to the outside of the laundry washing machine 200. In this manner, the processing unit of the detection unit 210 is ready for the subsequent detection.

As described above, the laundry washing machine 200 can concurrently perform detection of the substance that requires a certain period of time (step S309) and does a wash (step S312).

Note that steps S315 and S316 are not essential for the embodiment of the present disclosure. These steps are only example of use of the result of detection of a component performed in step S313. Unlike simple detection of a substance using only the level of dirt of wash water, the substance can be more accurately detected if the processes in steps S315 and S316 are performed. Thus, a more suitable wash can be done in accordance with the substance responsible for the dirt.

Figure 3:
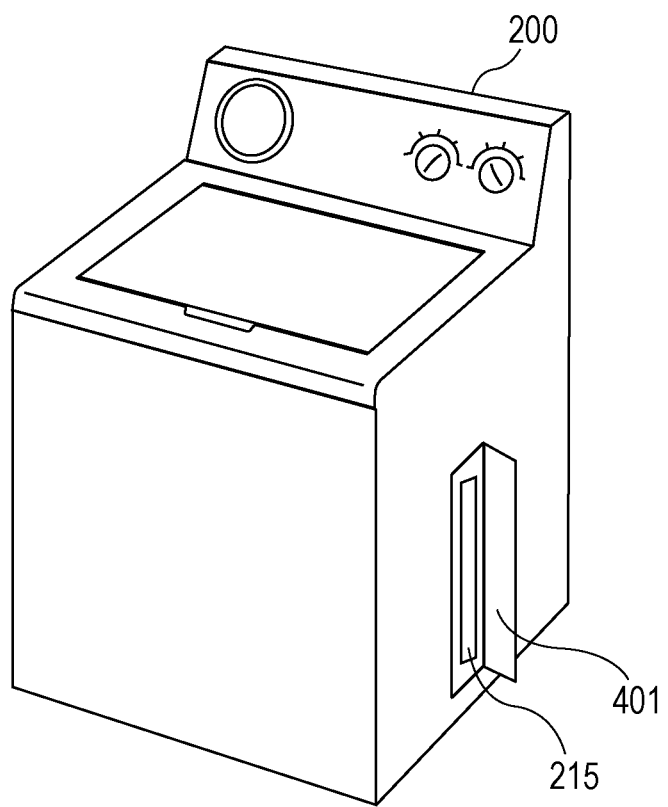
FIG. 3 is an external view illustrating an example of the configuration of the laundry washing machine according to the first exemplary embodiment.

FIG. 3 is an external view illustrating an example of the configuration of the laundry washing machine according to the first exemplary embodiment. If, as described above, component detection for the substance is performed by the detection unit 210 (the detector 216) using liquid chromatography, the column 215 may need to be periodically replaced with a new one. Accordingly, as illustrated in FIG. 3, a window 401 for replacement of the column is provided in the side surface of the laundry washing machine 200 so that replacement of the column 215 is facilitated. In this manner, the first exemplary embodiment becomes more preferable.

In this configuration, a technique for detecting the predetermined substance contained in the water stored in the tank 212 is not limited to liquid chromatography. For example, the predetermined substance may be detected using the pollen antigen detection technique described in Japanese Unexamined Patent Application Publication No. 2006-343134. In such a case, to supply an antibody fluorescent marker that reacts with the antigen, a cartridge containing the fluorescent marker may be replaced through the replacement window 401. In addition to this example, when some replaceable consumable needs to be used to accurately detect the predetermined substance, it is very effective for the present disclosure to form a replacement window at an appropriate position in the laundry washing machine 200.

According to the present exemplary embodiment, as can be seen from the timing diagram of FIG. 2, the control unit 220 sends the detection sample acquisition start signal to the detection unit 210 in only step S305. Accordingly, some of the water stored in the wash tub 202 is separated, and the predetermined substance contained in the separated water is detected only once. However, the configuration is not limited thereto. For example, by performing the process in step S305 at different timings, the control unit 220 can send the detection sample acquisition start signal to the detection unit 210 at different timings.

In this manner, upon receiving the detection sample acquisition start signal, the processing unit of the detection unit 210 can control the holding unit 213 to separate some of the water in the wash tub 202 and hold the separated water in the holding unit 213 at different timings. Thereafter, the detection unit 210 can detect the predetermined substance contained in the water held by the holding unit 213 at different timings.

In the following configuration, there may be one or multiple tanks 212. That is, the control unit 220 performs the process in step S305 and sends a first detection sample acquisition start signal to the detection unit 210. Thereafter, the detection unit 210 completes detection of the predetermined substance, and the tank 212 drains the water held by the tank 212 to the outside of the laundry washing machine 200. Subsequently, the control unit 220 performs the process in step S305 and sends a second detection sample acquisition start signal to the processing unit of the detection unit 210.

In contrast, in the following configuration, multiple tanks 212 are needed, and some of the water separated from the water in the wash tub 202 at different timings needs to be stored in different tanks 212. That is, during the period of time from the time the control unit 220 sends a first detection sample acquisition start signal to the detection unit 210 to the time the detection unit 210 completes detection of the predetermined substance and the tank 212 drains the water held by the tank 212 to the outside of the laundry washing machine 200, the control unit 220 sends a second detection sample acquisition start signal to the detection unit 210. This is because mixture of the water separated from the water in the wash tub 202 at different timings in only one tank 212 needs to be avoided.

The tap water used for the wash cycle in different areas may contain different components (e.g., the water may be hard water or soft water). If such a difference in contained component is not taken into account in advance, a component detection error may occur. For example, if the water supplied from the water mains 208 is hard water, the result of detection output to the detection unit 210 indicates a large amount of a substance contained in hard water, such as calcium carbonate. That is, a substance other than the substance attached to the laundry that is to be detected is included in the result of detection. Note that calcium carbonate does not contribute to estimation of the health condition of the user. Accordingly, it is desirable that a substance other than the substance attached to the laundry (i.e., a substance contained in the tap water) be not included in the result of detection output from the detection unit 210. To address such an issue, it is desirable that some of the water in the wash tub 202 be separated at different timings and be held by the holding unit 213 so that the predetermined substance contained in the water held by the holding unit 213 is detected at each of the different timings.

For example, after the processing unit of the washing unit 201 opens the valve V2 and dispenses tap water into the wash tub 202 and before a laundry is put into the wash tub 202, the control unit 220 sends a first detection sample acquisition start signal to the detection unit 210. The detection unit 210 opens the valve V3 and dispenses the water in the wash tub 202 into the tank 212 and, thereafter, closes the valve V3. In this manner, only the water supplied from the water mains 208 is held in the tank 212 of the holding unit 213. Subsequently, the detection unit 210 supplies the water held by the tank 212 to the column 215 and detects the substance contained in the water using the detector 216. Hereinafter, this detection is referred to as "detection A". The result of detection based on detection A (hereinafter referred to as "detection result A") includes the component information regarding the substance contained in the tap water.

Subsequently, for example, after the laundry is placed into the wash tub 202, the wash tub 202 agitates the laundry and the water. After a predetermined period of time has elapsed, the control unit 220 sends a second detection sample acquisition start signal to the detection unit 210. The detection unit 210 opens the valve V3 again and dispenses the water in the wash tub 202 into the tank 212 and, thereafter, closes the valve V3. In this manner, the substance contained in the tap water supplied from the water mains 208 and the substance that was attached to the laundry are contained in the water held by the tank 212 of the holding unit 213. Thereafter, the detection unit 210 supplies the water held by the tank 212 to the column 215 and detects the substances contained in the water using the detector 216. Hereinafter, this detection is referred to as "detection B", and the result of detection based on detection B is referred to as a "detection result B". The detection result B indicates the component information regarding the substance contained in the tap water and the component information regarding the substance attached to the laundry.

The detection unit 210 (e.g., the processing unit of the detection unit 210) compares the detection result A with the detection result B and identifies the component information regarding the substance contained in both the detection result A and detection result B as the component information regarding the substance contained in the tap water. Thereafter, the processing unit of the detection unit 210 removes the component information regarding the substance contained in the tap water from the detection result B and outputs the detection result to the control unit 220. In this manner, the result of detection sent to the control unit 220 includes only the component information regarding the substance attached to the laundry. Accordingly, the control unit 220 can analyze the received result of detection and generate the wash course information on the basis of the substance that was attached to the laundry (the predetermined substance).

While the above description has been made with reference to the processing unit of the detection unit 210 that compares the detection result A with the detection result B, identifies the component information regarding the substance contained in the tap water, and removes the component information regarding the substance contained in the tap water from the detection result B, the configuration is not limited thereto. For example, the control unit 220 may perform the above-described process. In such a case, the processing unit of the detection unit 210 sends the detection result A and the detection result B to the control unit 220. After receiving the detection result A and the detection result B, the control unit 220 can perform the above-described process. Even in this manner, the control unit 220 can identify the substance that was attached to the laundry as the predetermined substance and set the wash course on the basis of the predetermined substance.

Note that for example, immediately after the laundry is put into the wash tub 202 after the processing unit of the washing unit 201 opens the valve V1 and dispenses tap water into the wash tub 202, the control unit 220 may send a first detection sample acquisition start signal to the detection unit 210. The detection unit 210 opens the valve V3 and dispenses the water stored in the wash tub 202 to the tank 212 and, thereafter, closes the valve V3. It is highly likely that the substance attached to the laundry is not dissolved in the water in the wash tub 202 immediately after the laundry is put into the wash tub 202. Thus, even in this manner, it is highly likely that only the water supplied from the water mains 208 is stored in the tank 212 of the holding unit 213. Subsequently, the detection unit 210 delivers the water held by the tank 212 to the column 215 and detects the substance contained in the water using the detector 216. This detection may be referred to as "detection A". The detection result A based on detection A includes the component information regarding the substance contained in the tap water.

An example in which the water supplied from the water mains 208 is hard water is described below. Hard water contains calcium carbonate. Accordingly, in both detection A and detection B, calcium carbonate is detected. In detection A, the component of the substance that was attached to the laundry is not very well dissolved in the water. However, as the time passes, the component of the substance is dissolved in the water more and, therefore, the component of the substance is detected in detection B. Accordingly, the processing unit of the detection unit 210 compares the detection result A with the detection result B. The control unit 220 (the processing unit of the detection unit 210) identifies the component information regarding the substance detected in both the detection result A with the detection result B (e.g., calcium carbonate) as the component information regarding a substance contained in hard water and, thus, removes the component information regarding the identified substance from the detection result B. Thereafter, the control unit 220 (the processing unit of the detection unit 210) sends, to the control unit 220, a component detection completion signal including the result of detection B from which the component information regarding the substance identified (e.g., calcium carbonate) is removed.

The control unit 220 analyzes the received result of detection. Thus, the control unit 220 can generated the wash course information on the basis of the substance that was attached to the laundry (the predetermined substance) regardless of the quality of the tap water used to wash the laundry.

In addition, in detection B, the tap water may be heated using a heating unit, such as a heater (not illustrated), and the heated water may be used. By converting the cold tap water into heated water, the substance attached to the laundry is more easily separated. For example, in detection A, cold tap water is dispensed into the wash tub 202. During a period of time from the time detection A is carried out to the time detection B is carried out, the tap water in the wash tub 202 is heated into warm water. Thereafter, the control unit 220 may send a second detection sample acquisition start signal to the detection unit 210, and the detection unit 210 may carry out detection B. In this manner, the difference between the detection result A of detection A carded out using the cold tap water and the detection result B of detection B carried out using the warm tap water becomes large. Thus, the substance attached to the laundry can be more accurately detected.

The timing at which some of the water in the wash tub 202 is separated is not limited to the above-described timing. For example, by changing the timing at which some of the water in the wash tub 202 is separated, the substance attached to the laundry can be identified even after a laundry detergent is dispensed. The timing is described in detail below.

For example, immediately after the laundry detergent is dispensed into the wash tub 202 after the laundry 205 is put into the wash tub 202 and water is dispensed from the water mains 208 into the wash tub 202, the control unit 220 sends a detection sample acquisition start signal to the detection unit 210. The detection unit 210 opens the valve V3 and dispenses the water stored in the wash tub 202 into the tank 212. Thereafter, the detection unit 210 closes the valve V3. Thus, a substance contained in the tap water supplied from the water mains 208, the substance that was attached to the laundry, and a substance contained in the laundry detergent are contained in the water held by the tank 212 of the holding unit 213. Subsequently, the detection unit 210 supplies the water held by the tank 212 to the column 215 and detects the substance contained in the water using the detector 216. Hereinafter, this detection is referred to as "detection C". The result of detection based on detection C (hereinafter referred to as a "detection result C") includes the component information regarding the substance contained in the tap water, the component information regarding the substance attached to the laundry, and the component information regarding the substance contained in the laundry detergent.

Subsequently, after a predetermined period of time has elapsed since dispense of the laundry detergent, the control unit 220 sends a new detection sample acquisition start signal to the detection unit 210. The detection unit 210 opens the valve V3 and dispenses the water stored in the wash tub 202 into the tank 212 and, thereafter, closes the valve V3. In this manner, the substance contained in the tap water supplied from the water mains 208, the substance that was attached to the laundry, and the substance contained in the laundry detergent are contained in the water held by the tank 212 of the holding unit 213. Subsequently, the detection unit 210 supplies the water held by the tank 212 to the column 215 and detects the substances contained in the water using the detector 216. Hereinafter, this detection is referred to as "detection D". The result of detection based on detection D (hereinafter referred to as a "detection result D") includes the component information regarding the substance contained in the tap water, the component information regarding the substance attached to the laundry, and the component information regarding the substance contained in the laundry detergent.

The detection unit 210 (e.g., the processing unit of the detection unit 210) compares the detection result C with the detection result D and identifies the component information regarding the substance contained in both the detection result C and the detection result D and having a difference between the detected amounts, which is smaller than a predetermined value, as the component information regarding the substance contained in the tap water and the component information regarding the substance contained in the laundry detergent. Thereafter, the detection unit 210 removes the component information regarding the identified substance contained in the tap water and the component information regarding the identified substance contained in the laundry detergent from the detection result D. In this manner, the detection result D from which the component information regarding the above-described substances has been removed includes the component information regarding the substance attached to the laundry.

Alternatively, the detection unit 210 (e.g., the processing unit of the detection unit 210) compares the detection result C with the detection result D and identifies the component information regarding the substance contained in both the detection result C and the detection result D and having a difference between the detected amounts, which is larger than a predetermined value, as the component information regarding the substance attached to the laundry.

Alternatively, the detection unit 210 (e.g., the processing unit of the detection unit 210) compares the detection result C with the detection result D and identifies the component information regarding the substance included in only the detection result D as the component information regarding the substance attached to the laundry. Thereafter, the processing unit of the detection unit 210 removes the component information other than the component information regarding the substance attached to the laundry from the component information regarding the substances included in the detection result D. Subsequently, the processing unit of the detection unit 210 outputs, to the control unit 220, the result of detection including only the component information regarding the substance attached to the laundry. Consequently, the control unit 220 can analyze the received result of detection and generate the wash course information on the basis of the substance that was attached to the laundry (the predetermined substance).

That is, the detection unit 210 carries out detection twice (detection C and detection D), that is, at a time the laundry detergent is dispensed and at a time a predetermined period has elapsed since the dispense of laundry detergent. Thereafter, the detection unit 210 compares the results of detection based on the two detections (the detection result C and the detection result D) with each other and removes the component of the substance contained in the laundry detergent. In this manner, the substance attached to the laundry can be identified regardless of the type of the dispensed laundry detergent. Note that some substance attached to the laundry is not easily dissolved in the tap water, but is easily dissolved in water containing the laundry detergent. Accordingly, by using the above-described process, the component information regarding the substance that is difficult to separate from the laundry without the laundry detergent can be identified.

While the above description has been made with reference to the processing unit of the detection unit 210 that compares the detection result C with the detection result D, identifies the component information regarding the substance contained in the laundry detergent, and identifies the substance attached to the laundry, the configuration is not limited thereto. For example, the control unit 220 may perform the above-described process. In such a case, the processing unit of the detection unit 210 may send the detection result C and the detection result D to the control unit 220. Upon receiving the detection result C and the detection result D, the control unit 220 can perform the above-described process. Even in such a case, the control unit 220 can identify the substance that was attached to the laundry as the predetermined substance and set the wash course on the basis of the predetermined substance.

In addition, it is more desirable that the tap water be heated into warm water when detection D is carried out. Furthermore, before detection C is carried out, detection B may be carried out using only the tap water prior to dispense of the laundry detergent. By comparing the detection result B with the detection result C, the processing unit of the detection unit 210 can identify the substance existing in the water prior to addition of the laundry detergent. If the processing unit of the detection unit 210 removes the component information regarding the identified substance from the detection result C, the processing unit of the detection unit 210 can identify the component information regarding a new detected substance using the detection result C (e.g., the component information regarding the substance contained in the laundry detergent).

Furthermore, by comparing the detection result B, the detection result C, and the detection result D with one another in a similar manner, the processing unit of the detection unit 210 can identify the component information regarding the substance detected using the detection result D. In this manner, the component information regarding a new substance detected over time can be accurately identified. That is, the component information regarding the substance already detected can be more accurately removed over time.

The above-described detections C and D may be carried out twice using different laundry detergents. For example, a laundry detergent X is added. Immediately after the laundry detergent X is added, detection C is carried out. After a predetermined period of time has elapsed, the detection D is carried out. Furthermore, a laundry detergent Y is added. Immediately after the laundry detergent Y is added, detection E is carried out. After a predetermined period of time has elapsed, detection F is carried out. Both the result of detection based on detection E (the detection result E) and the result of detection based on detection F (the detection result F) indicate detection of the component information regarding the substance contained in the laundry detergent X and the component information regarding the substance contained in the laundry detergent Y. The component information regarding these substances can be identified by comparing the detection result E with the detection result F.

Comparison of the component information regarding the substance included in the detection result D and the component information regarding the substance included in the detection result F indicates that the detection result F includes the component information regarding a new substance that separated from the laundry due to addition of the laundry detergent Y. That is, the new substance detected in detection F cannot be separated by the laundry detergent X, but can be separated by the laundry detergent Y. Accordingly, if the component of the substance contained in the laundry detergent Y is already known, such a particular effect that the component information regarding the substance attached to the laundry 205 is more accurately identified can be obtained.

While the above description has been made with reference to the processing unit of the detection unit 210 that identifies the component information regarding the substance attached to the laundry 205 on the basis of comparison of the detection results C to F, the configuration is not limited thereto. For example, the control unit 220 may perform the above-described process.

While the first exemplary embodiment has been described with reference to acquisition of the water solution in the wash tub using the tank 212, the tank 212 is not an essential constituent element if a substance detection technique using the above-described time difference is employed. That is, the water solution having a laundry detergent added thereto can be delivered to the column 215 without storing the water solution in the tank 212. Thereafter, the substances can be detected using the detector 216. After a predetermined period of time has elapsed, the water solution in the wash tub 202 can be delivered to the column 215 without storing the water solution in the tank 212 again. The substances can be detected using the detector 216. Subsequently, by comparing two results of detection with each other, the component information regarding the substance contained in the laundry detergent can be removed from the result of detection. Thus, the substance separated from the laundry can be identified. According to the configuration, the object of the present disclosure, that is, detection of the predetermined substance attached to the laundry and washing of the laundry can be concurrently carried out without using the tank 212.

While the above description has been made with reference to detection of a substance using the above-described time difference and performed every time a wash cycle is carried out, the detection may be performed at another timing. For example, when the laundry washing machine is purchased, the control unit 220 sends a detection sample acquisition start signal to the detection unit 210 without laundry and a laundry detergent added therein. The detection unit 210 opens the valve V3 and dispenses the water stored in the wash tub 202 into the tank 212. Thereafter, the detection unit 210 closes the valve V3. In this manner, only the water supplied from the water mains 208 is held in the tank 212 of the holding unit 213. Subsequently, the detection unit 210 supplies the water held by the tank 212 to the column 215 and detects the substance contained in the water using the detector 216. Hereinafter, this detection is referred to as "tap water detection". The result of detection based on tap water detection (the tap water detection result) includes the component information regarding the substance contained in the tap water. If the tap water in the area in which the laundry washing machine is purchased is hard water, calcium carbonate, for example, is detected in this inspection. For example, the processing unit of the detection unit 210 records the tap water detection result in, for example, a memory (not illustrated). Thereafter, the processing unit of the detection unit 210 compares the result of detection of the substance obtained from a wash cycle with the tap water detection result and identifies the component information regarding the substance contained in the tap water. Subsequently, the processing unit of the detection unit 210 sends, to the control unit 220, a component detection completion signal including the result of detection from which the component information regarding the substance contained in the tap water is removed.

In this manner, the control unit 220 can generate wash course information on the basis of the component information regarding the substance attached to the laundry included in the result of detection. In addition, since the control unit 220 does not generate the wash course information using the component information regarding the substance contained in hard water, a detection error caused by the hardness of tap water can be prevented. Furthermore, if the tap water is hard water, the result of detection of a substance is influenced. In addition, unsatisfactory wash result due to, for example, not-functioning laundry detergent is caused. Accordingly, if it is determined that the tap water is hard water in the tap water inspection, the laundry washing machine 200 may give the user a message indicating that for example, the tap water should pass through a filter that converts hard water into soft water. Alternatively, hard water can be turned into soft water if the hard water is boiled. Accordingly, if it is determined that the tap water is hard water in the tap water inspection, the laundry washing machine 200 may boil the tap water and, thereafter, use the water for washing.

The above-described detection of a component of a substance contained in the tap water dispensed into the wash tub 202 may be periodically carried out in addition to at the point of purchase of the laundry washing machine 200. If the result of detection of a component of the substance contained in the tap water dispensed into the wash tub 202 (the result of tap water detection) at the point of purchase is compared with the result of the subsequent periodical detection of a component contained in the tap water dispensed into the wash tub 202, a substance that is not detected at the point of purchase (e.g., a substance produced by stains and mold or mildew in the wash tub 202) can be detected. Accordingly, the laundry washing machine 200 can present, to the user, the level of dirt of the wash tub 202 and a recommendation to clean the wash tub 202.

As described above, according to the present exemplary embodiment, the laundry washing machine 200 detects a predetermined substance in the water that is separated from the water in the wash tub 202 and that contains a substance dissolved therein. To detect the predetermined substance, a detection technique, such as liquid chromatography, is employed. The detection technique requires a certain length of time to detect the predetermined substance. If some of the water is not separated from the wash tub 202, a laundry detergent cannot be dispensed until the result of detection of the predetermined substance is obtained. Since the laundry washing machine 200 according to the present exemplary embodiment of the present disclosure separates some of the water containing a substance to be detected from the wash tub, the laundry detergent can be dispensed into the wash tub 202 without waiting for the result of detection being obtained. Thus, the laundry washing machine 200 can efficiently detect the predetermined substance that originates from the human body or the environment.

In addition, the laundry washing machine 200 detects the predetermined substance attached to the laundry during washing time of the laundry. In this manner, the laundry washing machine can detect the predetermined substance concurrently with the washing of the laundry. Thus, the need for a period of time dedicated to detection of the predetermined substance can be eliminated. As a result, the laundry washing machine 200 can efficiently detect the substance which originates from the human body or the environment.

In addition, the laundry washing machine 200 actively dissolves the substance that was attached to the laundry in the water and separates some of the water having the substance dissolved therein. Thereafter, the laundry washing machine 200 detects the predetermined substance in the separated water. Thus, the laundry washing machine 200 can more accurately detect the substance which originates from the human body or the environment.

In addition, by controlling, in particular, the wash tub 202, the laundry detergent dispenser, the holding unit 213, and the detection unit 210, the laundry washing machine can provide effects that are the same as the above-described effects.

In addition, the laundry washing machine 200 changes the setting for wash to more suitable setting on the basis of the result of detection of the predetermined substance. Thus, the laundry washing machine 200 can more thoroughly wash away the predetermined substance attached to the laundry.

In addition, the laundry washing machine 200 changes the setting for wash to more suitable and specific setting on the basis of the result of detection of the predetermined substance. Thus, the laundry washing machine 200 can more thoroughly wash away the predetermined substance attached to the laundry.

In addition, the laundry washing machine particularly 200 detects the substance floating in the air as the predetermined substance. The user can be aware of the result of detection of the substance floating in the air. Thus, the user can take an action that protects themselves on the basis of the result of detection. For example, the user can determine if they wear a mask or a cap or not, depending on the amount of the predetermined substance.

In addition, the laundry washing machine 200 particularly detects the antigen present in a pollen as the predetermined substance. The user can be aware of the result of detection of the antigen present in the pollen. Thus, the user can take an action that protects themselves on the basis of the result of detection. For example, the user can determine if they wear a mask or a cap or not, depending on the amount of the antigen present in the pollen.

In addition, the laundry washing machine 200 particularly detects a substance which originates from the human body as the predetermined substance. The user can be aware of the result of detection of the substance which originates from the human body. Thus, the user can take an action on the basis of the result of detection. For example, the user starts health management, such as starting exercising or food control, depending on the amount of the substance which originates from the human body.

In addition, the laundry washing machine 200 detects the predetermined substance using, in particular, liquid chromatography. Thus, the laundry washing machine 200 can more accurately detect the predetermined substance.

In addition, the laundry washing machine allows a part used for detecting the predetermined substance to be replaced through the window. The user can replace the part with a new one in a simpler way without disassembling the laundry washing machine.

In addition, the laundry washing machine 200 can dispense the water stored in the wash tub into the tank 212 and, thereafter, separate some of the water in the tank 212 from the water in the wash tub 202 using, in particular, a valve V3. Thus, the laundry washing machine 200 can more reliably separate, from the water in the wash tub 202, some of the water from which the predetermined substance is to be detected and, thereafter, detect the predetermined substance.

Second Exemplary Embodiment

Overall Configuration

The overall configuration of an attached substance detection system 10 according to a second exemplary embodiment is described first.

Figure 4:
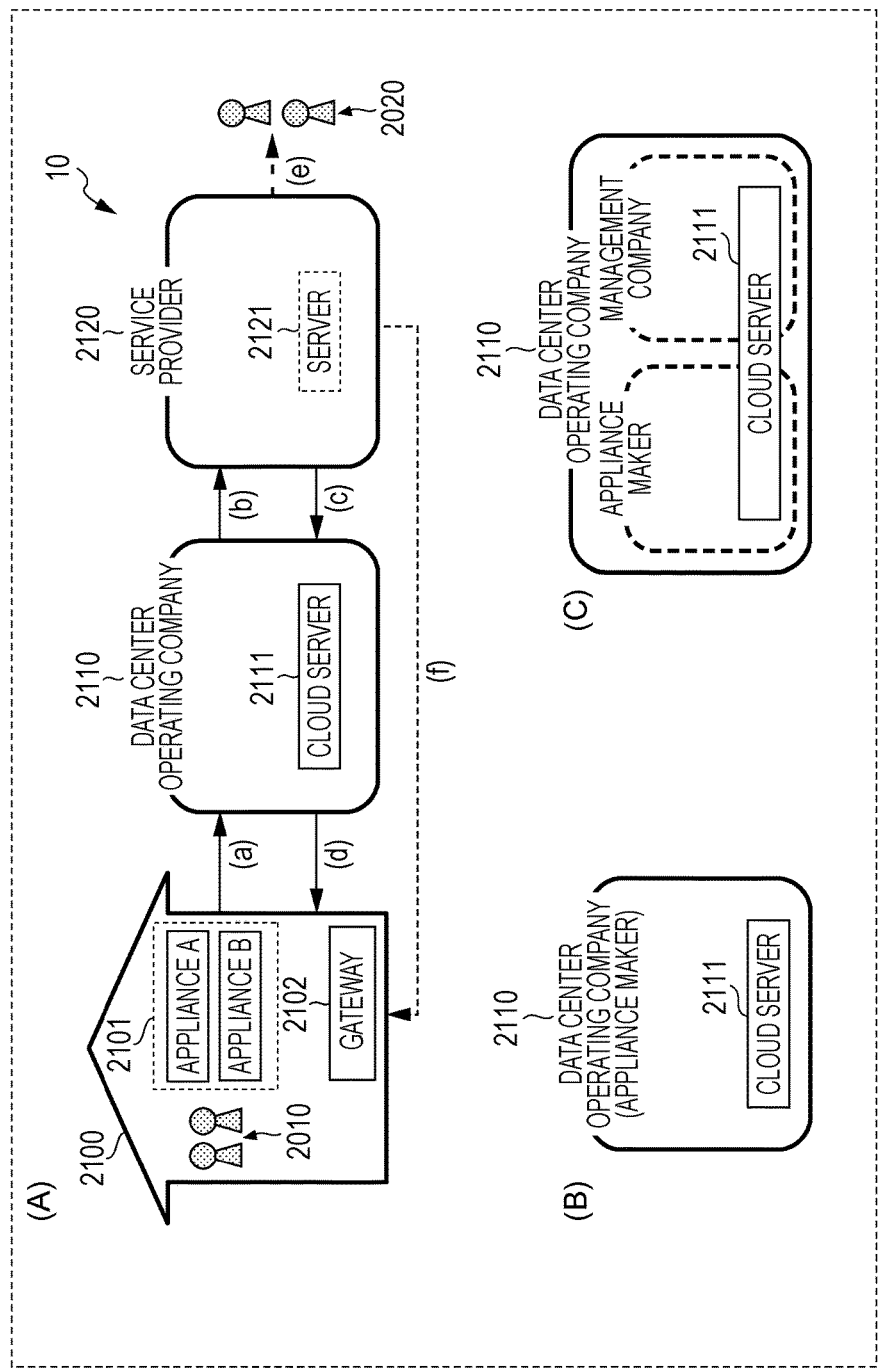
FIG. 4 is a block diagram of the overall configuration of the attached substance detection system according to a second exemplary embodiment.

FIG. 4 is a block diagram of the overall configuration of the attached substance detection system 10 according to the present exemplary embodiment.

As illustrated in FIG. 4(A), the attached substance detection system 10 includes a group 2100, a data center operating company 2110, and a service provider 2120.

The group 2100 is, for example, a company, an organization, or a household, and may be of any size. The group 2100 includes an appliance A and an appliance B, which are appliances of a plurality of appliances 2101, and a home gateway 2102. Examples of the appliances 2101 include a television set, an air conditioner, a laundry washing machine, and a microwave oven installed in a household. Some of the appliances 2101 are directly connectable to the Internet (e.g., a television set), and some of the appliances 2101 are not directly connectable to the Internet (e.g., an air conditioner). Even among the appliances that are not directly connectable to the Internet, some may be connected to the Internet via the home gateway 2102. In addition, the group 2100 includes a user 2010 who uses a plurality of the appliances 2101.

The data center operating company 2110 has a cloud server 2111 disposed therein. The cloud server 2111 is a virtual server that works with a variety of appliances via the Internet. The cloud server 2110 mainly manages a vast amount of data that is difficult to handle with, for example, ordinary database management tools (i.e., big data). The data center operating company 2110 performs management of data and management of the cloud server 2111 and operates a data center for managing the data and the cloud server 2111. The services provided by the data center operating company 2110 are described in more detail below.

Note that the data center operating company 2110 is not limited to a company that performs only management of data and management of the cloud server 2111. For example, if an appliance maker that develops and manufactures one of the appliances 2101 also performs management of data and management of the cloud server 2111, the appliance maker corresponds to the data center operating company 2110 (refer to FIG. 4(B)). In addition, the data center operating company 2110 is not limited to only one company. For example, if the appliance maker and another management company perform management of data or operate the cloud server 2111 in a mutual or shared manner, one or both of the appliance maker and another management company corresponds to the data center operating company 2110 (refer to FIG. 4(C)).

The service provider 2120 owns a server 2121. The server 2120 is of any size. For example, a memory of a personal PC may serve as the server 2121. Alternatively, in some cases, the service provider 2120 does not own the server 2121.

Note that the home gateway 2102 is not always necessary for the above-described system. For example, if the cloud server 2111 manages all the data, the need for the home gateway 2102 can be eliminated. In addition, as the case in which all of appliances in a household are connected to the Internet, there is a case in which an appliance that cannot be connected to the Internet by itself does not exist.

The flow of information in the above-described system is described below.

The appliance A or the appliance B of the group 2100 sends log information to the cloud server 2111 of the data center operating company 2110. The cloud server 2111 accumulates the log information regarding the appliance A or the appliance B (refer to an arrow (a) of FIG. 4). The log information is acquired by the appliances 2101 and represents, for example, information regarding the operation performed on each of the appliances 2101 by the user 2010 and information input to the appliances 2101 through the operation performed by the user 2010. For example, when the user 2010 uses a video on demand (VOD) service with a television set, the user 2020 operates the television set and inputs the personal information regarding the user 2010. Such personal information may be accumulated as the log information.

In addition, examples of the log information includes the dates on which the user 2010 turns on and turns off the television set, turns the channels, and operates the volume. Furthermore, examples of the log information include the dates on which the user 2010 opens the door of a refrigerator, turns on an air conditioner, and operates a microwave oven. The log information may be directly provided from each of the appliances 2101 to the cloud server 2111 via the Internet. Alternatively, the log information from each of the appliances 2101 may be temporarily accumulated in the home gateway 2102 and, thereafter, may be provided from the home gateway 2102 to the cloud server 2111.

Subsequently, the cloud server 2111 of the data center operating company 2110 provides the accumulated log information to the service provider 2120 by dividing the accumulated log information into predetermined lengths. The length of the log information may be a length with which the data center operating company can organize the accumulated information and provide the information to the service provider 2120 or a length requested by the service provider 2120. Note that the predetermined length need not be always fixed. That is, the amount of information provided may be changed as needed.

The log information is stored in the server 2121 of the service provider 2120 as needed (refer to an arrow (b) of FIG. 4). Thereafter, the service provider 2120 organizes the log information into information that suits for the service provided to the user, and the information is provided to the user. That is, the user may be the user 2010 who uses a plurality of the appliances 2101 or a user 2020 outside the group. The service may be directly provided from, for example, the service provider to the user (refer to arrows (e) and (f) of FIG. 4).

Alternatively, the service may be provided to the user via, for example, the cloud server 2111 of the data center operating company 2110 again (refer to arrows (c) and (d) of FIG. 4). Still alternatively, the cloud server 2111 of the data center operating company 2110 may organize the log information into information that suits for the service provided to the user, and the information may be provided to the service provider 2120. Note that the user 2010 may be the same as the user 2020 or be different from the user 2020.

Detailed Configuration

Figure 5:
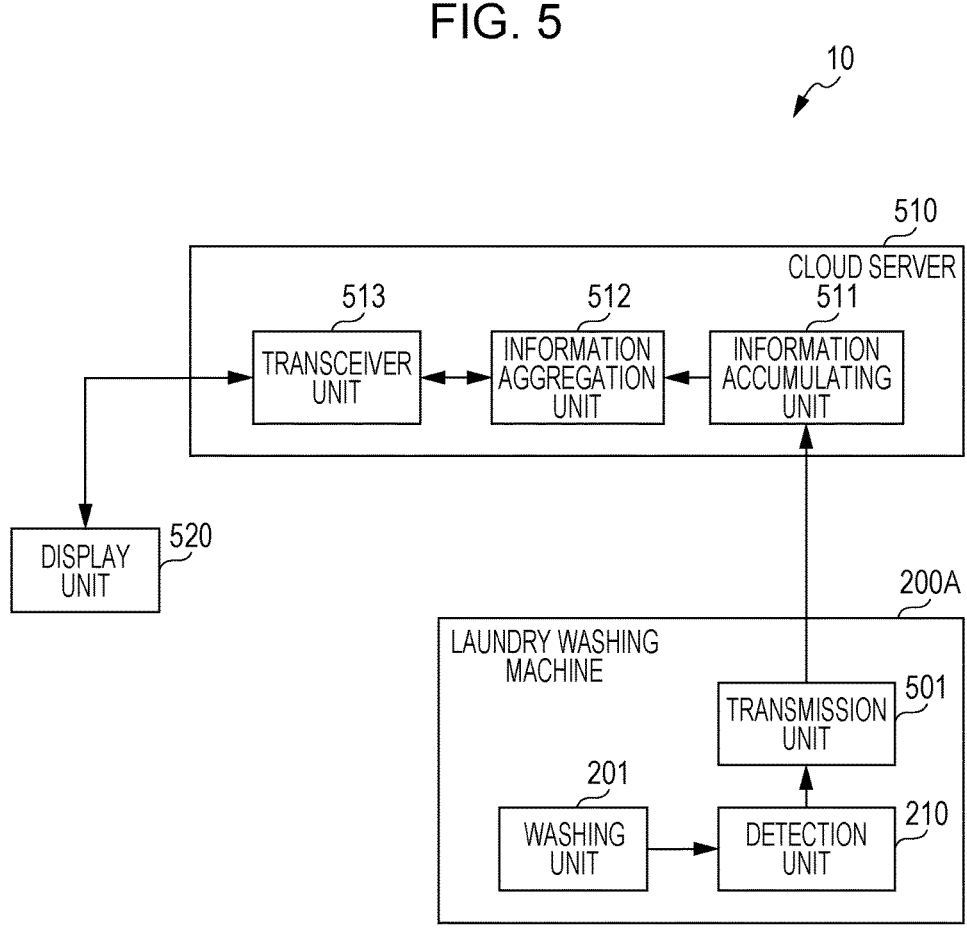
FIG. 5 is a block diagram of the detailed configuration of the attached substance detection system according to the second exemplary embodiment.

FIG. 5 is a block diagram of the detailed configuration of the attached substance detection system 10 according to the present exemplary embodiment. Note that in FIG. 5, constituent elements similar to those described above are identified with the same reference numerals, and description of the constituent elements is not repeated.

As illustrated in FIG. 5, the attached substance detection system 10 includes a laundry washing machine 200A, a cloud server 510, and a display unit 520.

The laundry washing machine 200A corresponds to the appliance A or the appliance B (2101) included in the group 2100 illustrated in FIG. 4.

The laundry washing machine 200A includes the washing unit 201, the detection unit 210, the control unit 220 (not illustrated), and a transmission unit 501. Unlike the laundry washing machine 200 according to the first exemplary embodiment, the laundry washing machine 200A includes the transmission unit 501.

The transmission unit 501 sends, to the cloud server 510, the component information regarding the substance attached to laundry, which corresponds to the result of detection performed by the detection unit 210. Note that the transmission unit 501 may additionally have a function of receiving information from the cloud server 510 so as to serve as a transceiver unit.

The cloud server 510 corresponds to the cloud server 2111 illustrated in FIG. 4. Preferably, the cloud server 510 is a server on the Internet and is disposed at a location other than the house where the laundry washing machine 200A is installed (the group 2100). However, the location is not limited thereto. For example, the cloud server 510 may be disposed in, for example, the house where the laundry washing machine 200A is installed. In addition, the constituent elements of the cloud server 510 (described in more detail below) and, in particular, an information accumulating unit 511 and an information aggregation unit 512, may be incorporated into the laundry washing machine 200A.

The cloud server 510 includes the information accumulating unit 511, the information aggregation unit 512, and a transceiver unit 513. Note that since the cloud server 510 is an apparatus that is located outside the laundry washing machine 200A and is connected to the laundry washing machine 200A via a network, such as the Internet, the cloud server 510 is also referred to as an "external apparatus".

The information accumulating unit 511 accumulates the component information by storing the component information in a writable recording medium. Example of the writable recording medium include a hard disk and a memory. Every time the detection unit 210 outputs the component information corresponding to the result of detection, the information accumulating unit 511 accumulates the component information in association with the time at which the component information is output. By storing the component information regarding at least two washes using the information accumulating unit 511, the temporal variation of the component information can be analyzed.

The information aggregation unit 512 is a processing unit that reads out a plurality of pieces of the component information from the information accumulating unit 511 in response to a request from the display unit 520 (described in more detail below), analyzes the temporal variation of the pieces of the component information, and generates display information. The display information is written in, for example, the HyperText Markup Language (HTML) and is displayed using, for example, a Web browser.

The transceiver unit 513 is a processing unit that receives a request for the display information from the display unit 520. In addition, the transceiver unit 513 sends the display information to the display unit 520 in response to a request.

The display unit 520 is a display screen (a display) used to display, for example, the component information. The display unit 520 may be provided in the laundry washing machine 200A or a terminal device, such as a smartphone, a tablet, or a personal computer (PC), that is connected to the cloud server 510 via a network, such as the Internet. The display unit 520 sends a request to the cloud server 510 on the basis of the operation performed by the user, receives the display information, and displays the display information using, for example, the Web browser.

That is, the display unit 520 displays each of the plurality of pieces of information accumulated in the information accumulating unit 511 in association with the time at which the information was output.

As used herein, an apparatus including the display unit 520 is also referred to as an "external display terminal". The external display terminal includes, for example, a reception unit (not illustrated) that receives information sent from the cloud server 510 and the laundry washing machine 200A via a network. In addition, the external display terminal may include a transmission unit (not illustrated) that sends information to, for example, the cloud server 510 and the laundry washing machine 200A. Alternatively, the display unit 520 may be provided in the laundry washing machine 200A.

Method for Detecting Substance Attached to Laundry

A particular operation performed by the clothing attached substance detection system having the above-described configuration according to the present exemplary embodiment (an attached substance detecting method) is described below.

Figure 6:
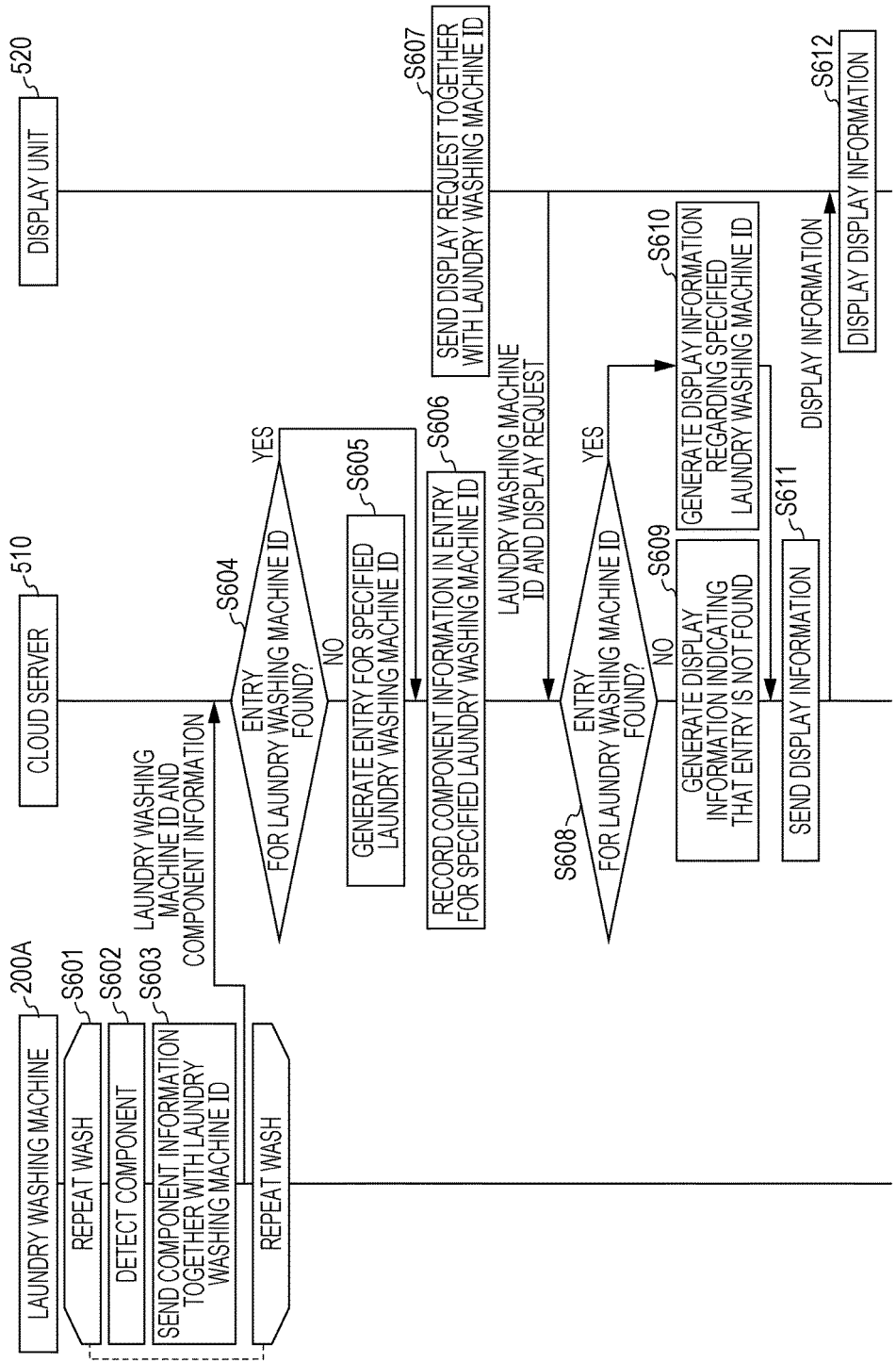
FIG. 6 is a sequence diagram of an attached substance detecting method according to the second exemplary embodiment.

FIG. 6 is a sequence diagram illustrating the operation performed by the attached substance detecting method according to the present exemplary embodiment.

In step S601, the laundry washing machine 200A repeatedly does a wash. In general, the laundry washing machine 200A does wash once or twice a day and repeats the wash every day. In this manner, the laundry washing machine 200A repeatedly does wash. Note that the number of washes varies with the household profile. Three or more washes a day are done in some household, and one wash a day is done in some household.

In step S602, the detection unit 210 detects a substance attached to the laundry during washing as described in the first exemplary embodiment. Thereafter, the detection unit 210 outputs, to the transmission unit 501, the component information of the predetermined substance separated from the laundry, that is, the result of detection.

In step S603, the control unit 220 causes the transmission unit 501 to send, to the cloud server 510, the result of detection including the component information together with a laundry washing machine ID, which is an ID unique to each of the laundry washing machines 200A.

In step S604, the cloud server 510 receives the laundry washing machine ID and the component information. Thereafter, the cloud server 510 determines whether the entry for the received laundry washing machine ID is found in the information accumulating unit 511. If the entry is not found ("NO" in step S604), the processing proceeds to step S605. However, if the entry is found ("YES" in step S604), the processing proceeds to step S606.

In step S605, the information accumulating unit 511 generates a new entry for the received laundry washing machine ID.

In step S606, the information accumulating unit 511 records the received component information in the entry for the received laundry washing machine ID. Every time wash is done by the laundry washing machine 200A, the process in step S606 is performed.

In step S607, the display unit 520 sends a display request together with the laundry washing machine ID. By communicating information with the laundry washing machine 200A using some information transfer technique, the display unit 520 can obtain the laundry washing machine ID of the laundry washing machine 200A in advance. Examples of the information transfer technique include an information transfer technique using wireless communication, such as near field communication, and an information transfer technique using wired communication. Alternatively, the information transfer may be achieved by the user reading out the laundry washing machine ID die stamped on the laundry washing machine 200A and inputting the readout laundry washing machine ID to the display unit 520.

In step S608, upon receiving the laundry washing machine ID and the display request, the cloud server 510 determines whether the entry for the specified laundry washing machine ID is found in the information accumulating unit 511. If the entry is not found ("NO" in step S608), the processing proceeds to step S609. However, if the entry is found ("YES" in step S608), the processing proceeds to step S610.

In step S609, the information aggregation unit 512 generates display information indicating that the entry is not found.

In step S610, the information aggregation unit 512 reads out a plurality of pieces of the component information, analyzes the time series variation of each of the pieces of the component information, and generates display information.

In step S611, the transceiver unit 513 sends the display information to the display unit 520 that has sent the display request.

In step S612, the display unit 520 receives the display information and displays the display information. For example, in a case that display unit 520 is provided in the laundry washing machine 200A, in step S612, the control unit 220 causes the display unit 520 to display the display information.

Figures 7, 8:
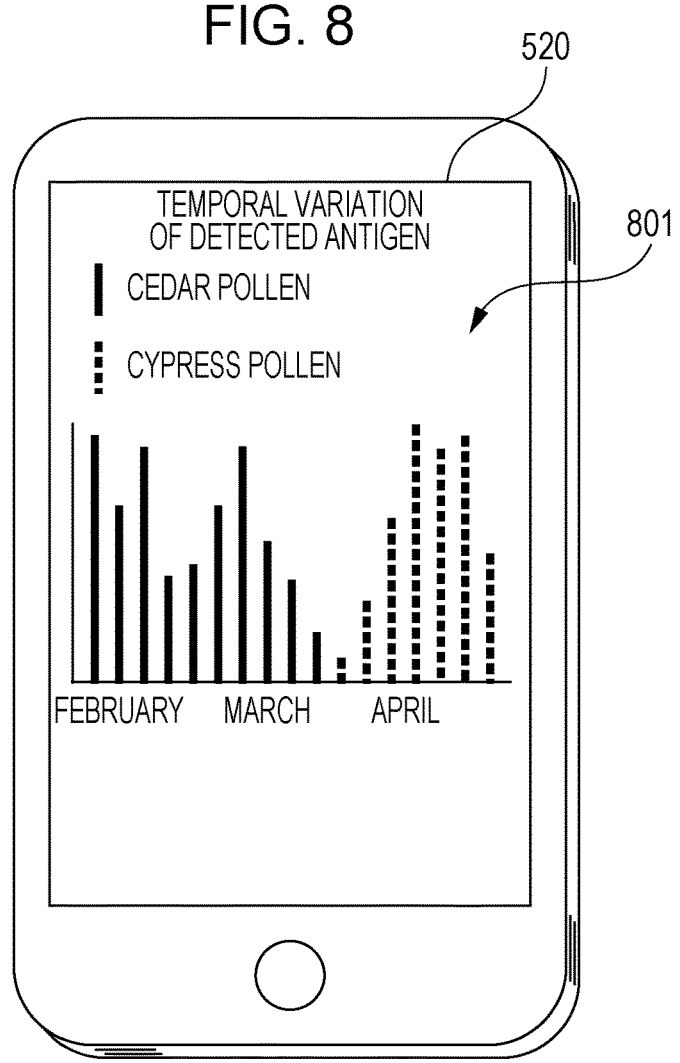
FIG. 7 illustrates an example of the component information for the attached substance detecting method according to the second exemplary embodiment.
FIG. 8 illustrates an example of a display image for the attached substance detecting method according to the second exemplary embodiment.

FIG. 7 illustrates an example of the component information for the attached substance detecting method according to the second exemplary embodiment. As described above, each of all the manufactured laundry washing machines 200A has a unique ID, and an entry for each of the IDs is generated in the information accumulating unit 511. The entry includes the amount of substances (e.g., A and B) detected by the laundry washing machine 200A for each of the washing dates. In FIG. 7, the pollen antigen is detected, for example.

The display information generated from such component information is described below.

FIG. 8 illustrates an example of a display image for the attached substance detecting method according to the present exemplary embodiment. The display image illustrated in FIG. 8 is displayed on the display unit 520. In FIG. 8, the temporal variation of the amount of the pollen antigen attached to the laundry for each of the washing dates is expressed in the form of a graph 801. By viewing the graph 801, the user can be aware that the pollen antigen, which causes allergies in themselves, is increasing or decreasing. By protecting themselves from pollen, the user can improve their health.

Note that a commercially available simple pollen sensor detects a pollen-like particle using a photosensor. Accordingly, it is difficult for the pollen sensor to detect whether the particle is a real pollen particle. In addition, the pollen sensor is not designed to detect a substance that causes pollen disease.

What the user really want is information regarding a substance that causes the user to have an allergic reaction. This information varies depending on the type of pollen, such as cedar pollen or cypress pollen. Accordingly, to obtain the information, the antigen need to be extracted from the pollen, and the component of the antigen needs to be analyzed. To extract the antigen from the pollen, water is required, and a complicated analyzing device is required. That is, it is significantly difficult to detect the pollen antigen in the household.

According to the present exemplary embodiment, the laundry washing machine 200A uses water to perform washing, which is an original function of laundry washing machines. Thus, by incorporating a device to detect the pollen antigen into the laundry washing machine 200A, the laundry washing machine 200A can advantageously generate the information regarding the antigen that the user really wants and allow the user to view the information.

According to the present exemplary embodiment, to improve the performance to detect the pollen antigen, the configuration is designed such that the component information is stored in the information accumulating unit 511 of the cloud server 510 and the temporal variation of the amount of pollen antigen is displayed. However, the configuration of the laundry washing machine 200A is not limited thereto. For example, the function of detecting the pollen antigen can be incorporated into the configuration according to the first exemplary embodiment. In such a case, since the information accumulating unit 511 is not provided, it is difficult to display the temporal variation of the amount of the pollen antigen. However, by displaying the detected amount of the antigen every time wash is done, the health conditions of the user can be increased. Alternatively, if the laundry washing machine 200 described in the first exemplary embodiment has a configuration including the information accumulating unit 511 and the information aggregation unit 512, the temporal variation of the pollen antigen can be displayed.

According to the present exemplary embodiment, the display unit 520 displays the temporal variation of the amount of the pollen antigen for each of the laundry washing machines 200A that is specified by the laundry washing machine ID. Instead, the amounts of the pollen antigen detected by a plurality of the laundry washing machines 200A may be summed for each of predetermined areas, such as cities or towns. Thereafter, the temporal variation of the amount may be displayed. In this manner, the information regarding the pollen antigen that cannot be detected by the laundry washing machine 200A operated by the user can be compensated for by the information from the laundry washing machine 200A used in another household. Accordingly, the attached substance detection system can obtain more detailed pollen information.

In addition, the display unit 520 may display the information regarding the pollen antigen for each of the areas of the country. In such a configuration, since the user can be aware of the greater-lesser relationship of the amount of the pollen antigen among the areas, the user can protect themselves by, for example, cancelling their trip to an area where a large amount of the antigen that causes allergic reactions of the user is detected. Thus, the health conditions of the user can be increased.

In the above-described configuration, the attached substance detection system has the position information for each of the laundry washing machine IDs. The position information is use to identify in which area each of the laundry washing machines is installed. The position information may be a ZIP code. Alternatively, the position information may be a ZIP code that is registered in the laundry washing machine 200A and that is sent to the cloud server 510 together with the component information. Still alternatively, the position information may be information that is obtained from a global positioning system (GPS) incorporated into a device including the display unit 520 and that is sent to the cloud server 510 together with the component information. Yet still alternatively, the position information may be the position information that is registered in the appliances 2101 other than the laundry washing machine 200A in the group 2100 illustrated in FIG. 4. For example, the position information may be a ZIP code registered to receive an on-demand service using a television set.

As described above, according to the present exemplary embodiment, the laundry washing machine can appropriately display, on the display unit, the result of detection performed by the detection unit to present the result of detection to the user.

In addition, the laundry washing machine displays the temporal variation of the result of detection obtained through the plurality of washes. By viewing the information displayed by the laundry washing machine, the user can find out a temporal decrease or increase in the amount of the predetermined substance. In this manner, the user can take an action according to the temporal variation of the amount of the predetermined substance.

Third Exemplary Embodiment

According to the configurations of the above-described exemplary embodiments, the component information is aggregated for each of the laundry washing machines. According to the present exemplary embodiment, an attached substance detection system that increases the physical conditions and health conditions of an individual more by aggregating the component information for the individual who wore the laundry is described below.

Detailed Configuration

Figure 9:
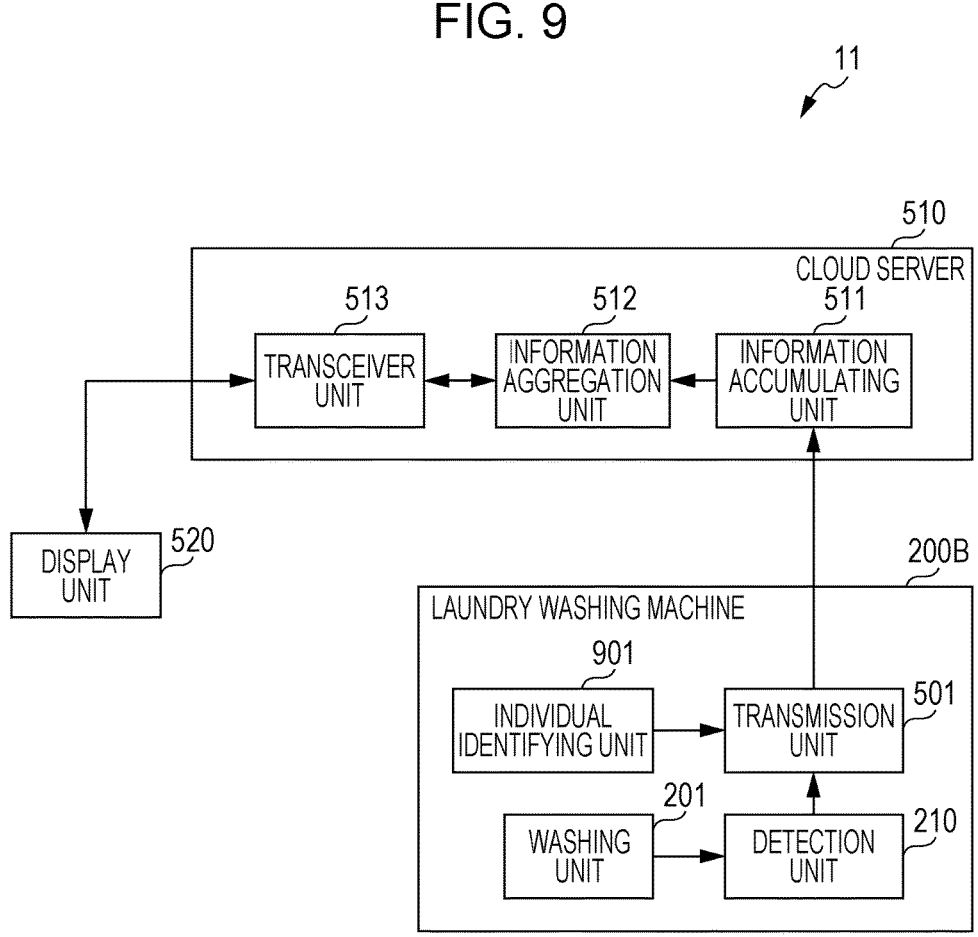
FIG. 9 is a block diagram of the detailed configuration of an attached substance detection system according to a third exemplary embodiment.

FIG. 9 is a block diagram of the detailed configuration of the attached substance detection system 11 according to a third exemplary embodiment. Note that in FIG. 9, constituent elements similar to those described above are identified with the same reference numerals, and description of the constituent elements is not repeated.

A laundry washing machine 200B includes the washing unit 201, the detection unit 210, the control unit 220 (not illustrated), the transmission unit 501, and an individual identifying unit 901. Unlike the laundry washing machine 200A according to the second exemplary embodiment, the laundry washing machine 200B includes the individual identifying unit 901.

The individual identifying unit 901 is a processing unit that identifies an individual who wore the laundry placed in the laundry washing machine 200B. The individual identifying unit 901 includes a touch panel that displays information and that receives an operation performed by a user.

The information accumulating unit 511 accumulates information in association with a personal ID indicating an individual identified by the individual identifying unit 901.

The display unit 520 receives a specified personal ID, which is the personal ID specified by the user. Thereafter, the display unit 520 reads out pieces of the information associated with the specified personal ID received from the information accumulating unit 511 and displays each of the pieces of the information in association with the time at which the piece of the information was output.

Figure 10A:
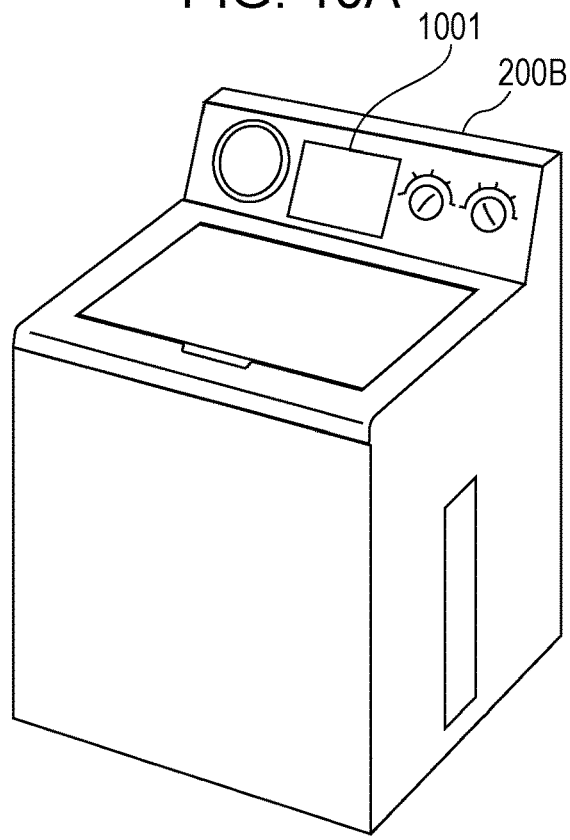
FIG. 10A is a schematic external view of a laundry washing machine that constitutes the attached substance detection system according to the third exemplary embodiment.
Figure 10B:
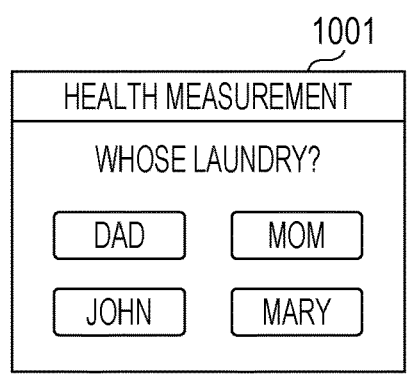
FIG. 10B illustrates an example of a display image displayed by the laundry washing machine that constitutes the attached substance detection system according to the third exemplary embodiment.

FIG. 10A is a schematic external view of the laundry washing machine 200B that constitutes the attached substance detection system according to the present exemplary embodiment. FIG. 10B illustrates an example of a display image displayed by the laundry washing machine 200B that constitutes the attached substance detection system according to the present exemplary embodiment.

The display image illustrated in FIG. 10B is an example of an image displayed on the display of the individual identifying unit 901 of the laundry washing machine 200B illustrated in FIG. 10A. The display includes a touch panel 1001.

As illustrated in FIG. 10B, the touch panel 1001 displays the display image for identifying one of pre-registered family members who wore the laundry. More specifically, the display image includes, for example, buttons that allow the user to select one of the family members "Dad", "Mom", "John", and "Mary". By touching one of the buttons in the display image, the user can select one of the family members. Note that by touching a plurality of the buttons at a time, a plurality of family members can be selected.

Note that if the display unit 520 is provided in a terminal device in the form of a touch panel, the touch panel 1001 may be implemented as the touch panel of the terminal device.

Method for Detecting Substance Attached to Laundry

A particular operation performed by the clothing attached substance detection system having the above-described configuration according to the present exemplary embodiment (an attached substance detecting method) is described below.

FIG. 11 is a sequence diagram illustrating the operation performed by the attached substance detecting method according to the present exemplary embodiment.

In step S601, the laundry washing machine 200B repeatedly does a wash.

In step S1201, when washing is started, an individual who wore the laundry is identified by the individual identifying unit 901, and a personal ID that is pre-registered so as to be unique is generated.

In step S602, the detection unit 210 detects a substance attached to the laundry during washing as described in the first exemplary embodiment. Thereafter, the detection unit 210 outputs, to the transmission unit 501, the component information of the predetermined substance separated from the laundry, that is, the result of detection.

In step S1202, the control unit 220 causes the transmission unit 501 to sends, to the cloud server 510, the component information together with the laundry washing machine ID, which is unique to each of the laundry washing machines 200B, and the personal ID.

In step S1203, the cloud server 510 receives the laundry washing machine ID, the personal ID, and the component information. Thereafter, the cloud server 510 determines whether the entry for the received laundry washing machine ID and the personal ID is found in the information accumulating unit 511. If the entry is not found ("NO" in step S1203), the processing proceeds to step S1204. However, if the entry is found ("YES" in step S1203), the processing proceeds to step S1205.

In step S1204, the information aggregation unit 512 generates a new entry for the received laundry washing machine ID and the personal ID.

In step S1205, the information aggregation unit 512 records the received component information in the entry for the received laundry washing machine ID and personal ID. The process in step S1205 is performed every time a wash is done by the laundry washing machine 200B.

In step S1206, the display unit 520 sends a display request together with the laundry washing machine ID and the personal ID.

In step S1207, upon receiving the laundry washing machine ID, the personal ID, and the display request, the cloud server 510 determines whether the entry for the specified laundry washing machine ID and personal ID is found in the information accumulating unit 511. If the entry is not found ("NO" in step S1207), the processing proceeds to step S609. However, if the entry is found ("YES" in step S1207), the processing proceeds to step S610.

In step S609, the information aggregation unit 512 generates display information indicating that the entry is not found.

In step S610, the information aggregation unit 512 reads out a plurality of pieces of the component information, analyzes the time series variation of each of the pieces of the component information, and generates display information.

In step S611, the transceiver unit 513 sends out the display information to the display unit 520 that has sent the display request.

In step S612, the display unit 520 receives the display information and displays the display information. For example, in a case that display unit 520 is provided in the laundry washing machine 200B, in step S612, the control unit 220 causes the display unit 520 to display the display information.

FIG. 12 illustrates an example of a relationship between a substance attached to the laundry and a disease that is likely to be triggered by the substance.

For example, a large amount of acetone is produced and disposed of in the human body through metabolic abnormality. Accordingly, if acetone is attached to the laundry, it can be estimated that a person who wore the laundry is diabetic, obese, or on some unhealthy diet.

FIG. 13 illustrates an example of the component information in the attached substance detecting method according to the third exemplary embodiment. The information accumulating unit 511 generates an entry for each of the laundry washing machine IDs and the personal IDs. The entry has the recorded amount of the substance (e.g., A and B) detected by the laundry washing machine 200B on each of the washing dates. In FIG. 13, examples of the substance produced by the human body illustrated in FIG. 12 are shown.

Figure 14:
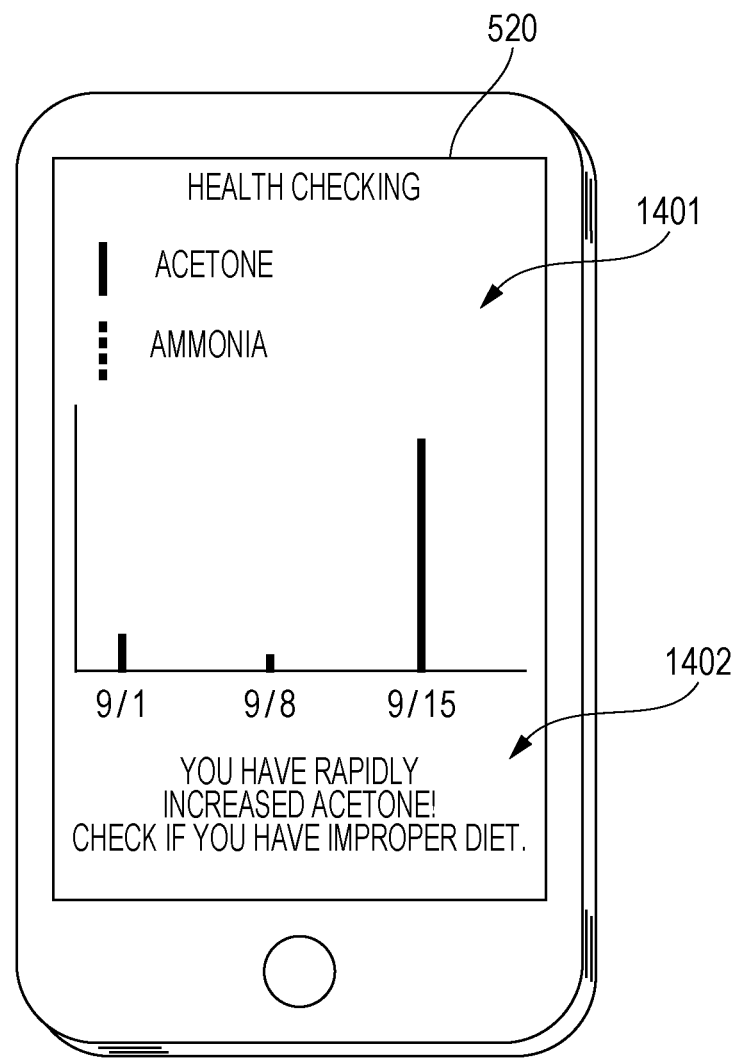
FIG. 14 illustrates an example of a display unit used by the attached substance detecting method according to the third exemplary embodiment.

An example of the display information generated from the component information and displayed on the display unit 520 is illustrated in FIG. 14.

That is, FIG. 14 illustrates an example of the display unit used for the attached substance detecting method according to the present exemplary embodiment. In this example, the temporal variation of the amount of the substance generated by the human body and attached to the laundry for each of the washing dates is expressed in the form of a graph 1401. In addition, the likely disease type estimated from the variation of the amount is displayed as an annotation 1402.

The annotation 1402 is a warning to the user, which indicates that the user may be in the state of starvation because of improper diet. In addition, the graph 1401 can be used by the user to recognize a change in their physical condition and the likeliness of disease and increase their health conditions.

While the present exemplary embodiment has been described with reference to the configuration including the individual identifying unit 901 for identifying individuals in order to increase the effect of personal health management, the configuration is not limited thereto. For example, in a single-person household or a household in which the laundry washing machine 200B is used for only an individual, the individual identifying unit 901 is not necessary. In addition, even in a household in which a laundry washing machine 200B is used for all family members, by detecting a substance specific to a certain disease and giving a warning indicating that any one of the family members may suffer from the disease, the health conditions of the family can be increased even if the individual identifying unit 901 is not provided.

While the present exemplary embodiment has been described with reference to the individual identifying unit 901 causing the user to touch a button for identifying an individual every time laundry is done, the configuration is not limited thereto. For example, the individual identifying unit 901 may identify an individual in first wash. In second and subsequent washes, the individual identifying unit 901 may compare a combination of the amounts of a plurality of detected substances produced by the human body with the component information for each individuals stored in the past and determine the individual having the combination of the amounts of substances having the highest similarity to be an individual who wore the current laundry. In such a case, the individual identifying unit 901 may display, to the user, a screen for confirming whether the individual determined by the individual identifying unit 901 is correct or not. In addition, a threshold value may be provided for the similarity. When the combination is compared with the component information regarding each individual and if the similarity is lower than the threshold value at all times, it is determined that identifying an individual is failed. Thus, the individual identifying unit 901 may display a request for identifying the individual to the user.

While the present exemplary embodiment has been described with reference to the configuration that creates the component information in an entry having the combination of the personal ID and the laundry washing machine ID in the information accumulating unit 511, the configuration is not limited thereto. The entry may be an entry that stores the laundry washing machine ID and, thus, is associated with only the personal ID. In such a case, the personal ID needs to be completely unique to each individual. In this configuration, even when the component is detected by different laundry washing machines 200B, the substance can be aggregated for the individual who wore the laundry. For example, the clothing of an individual is washed by a laundry washing machine in the household and is washed by a laundry washing machine at destination of a business trip, the amount of the substance can be stored for the individual. Thus, the information can be used as the health management regardless of the location at which the clothing is washed.

According to the present exemplary embodiment, the amount of the laundry from which a component is detected is not limited to any value. However, to more accurately record the temporal variation of the amount of the detected substance, it is desirable that the amount of the laundry from which the component is to be detected be the same at all times. In addition, it is desirable that a period of time during which the user wore the laundry be the same at all times. For example, it is ideal that the laundry washing machine 200B detect the component once in every morning for one underwear that was worn by the user on the previous day for all day long. After the component analysis becomes ready (refer to step S308 illustrated in FIG. 2), it is allowed to add the other laundry into the laundry washing machine 200B. Furthermore, it is more effective to display, on the display provided on the laundry washing machine 200B, a guidance message prompting the user to add laundry in the above-described manner (i.e., to place the underwear first and place the other laundry after the detection of the component is ready and before washing is started).

In addition, to normalize the amount of the substance with respect to the amount for one usual underwear when an unusual amount of the laundry is placed in the laundry washing machine 200B and the component is detected, the user interface that allows the user to input the amount of the laundry placed in the laundry washing machine 200B. Alternatively, instead of allowing the user to input the amount of the laundry, the load imposed on the motor 204 when the pulsator 203 is rotated (S303 of FIG. 2) may be measured before detection. Thus, the amount of the laundry may be estimated, and the amount of the substance may be normalized using the estimated amount of the laundry.

While the present exemplary embodiment has been described with reference to the configuration of the household laundry washing machine 200B that detects the substance that originates from the human body and that is attached to the laundry to increase the health conditions, the configuration is not limited thereto. For example, when a dry cleaning store washes laundry that a customer brings in, the dry cleaning store may detect a substance which originates from the human body and presents the graph 1401 illustrated in FIG. 14 to the customer. In this manner, the attached substance detection system may improve the health of the customer. In such a case, to present the temporal variation of the amount of the substance, the dry cleaning store holds the data of the substance that was attached to the laundry of the customer for a long time. Thus, to continuously receive the above-described health improving service, the customer negligibly uses another dry cleaning store, since another dry cleaning store does not have the historic data. To keep customers for a long time, this is a significantly effective service for dry cleaning stores. In addition, a dry cleaners chain may manage substance data for a customer. Even when the customer visits a different dry cleaning store of the same franchise chain, the dry cleaning store allows the customer to view the historic data. In such a configuration, even when the customer moves house, the customer needs to use a dry cleaning store of the same franchise chain. This is a significantly effective service of a business owner of the dry cleaning store of the franchise chain. Furthermore, the component information detected in the dry cleaning store and the component information detected by the laundry washing machine 200B in the household of the customer may be summed and be displayed. In such a case, even when the dry cleaning store is used and even when the laundry washing machine 200B in the household is used, the substance can be detected at all times and, thus, more accurate variation of the physical conditions can be found out. The dry cleaning store may be a store for general consumers or for industrial uses. For example, the dry-cleaning store may be a facility for cleaning working uniforms of the employees. In such a case, the enterprise can manage the information regarding the health conditions of the employees. In addition, by detecting substances attached to the working uniforms, the enterprise can determine if unsafe or unhealthful working conditions are present.

While the present exemplary embodiment has been described with reference to the configuration in which the information aggregation unit 512 of the cloud server 510 including a computer generates the graph 1401 and the annotation 1402 illustrated in FIG. 14, the configuration is not limited thereto. For example, the information aggregation unit 512 may have a configuration that detects an abnormal event of the temporal variation of the amount of the substance (e.g., the case in which when the variation is compared with a predetermined threshold value, an abrupt change that exceeds the threshold value occurs). If an abnormal event occurs, the information may be sent to a healthcare agency and ask for a decision of a medical doctor. In this case, the user can obtain advice for improving their health that is more accurate than that generated by a computer. In addition, the component information of an insured person under health insurance may be configured so as to be open for inspection by the insurance provider. The insurance provider examines the health conditions of the customer using the component information. If no abnormal indication is found in the component information, the insurance provider reduces the insurance premium. In this manner, the insurance provider can reduce the risk of loss, and the customer can have the reduced insurance premium, which are advantageous for both the insurance provider and the customer.

While the present exemplary embodiment has been described with reference to a temporal variation of the amount of the substance that originates from each of individuals and that is presented to the individual, the configuration is not limited thereto. For example, the temporal variation of the amount of the substance that originates from the human body of each of the individuals in a certain area, such as a city or a town, may be aggregated for the area, and the temporal variation of the amount may be displayed. In such a configuration, the characteristic of the physical conditions for the area can be found out and, thus, the action plan to promote the health of people in the area can be easily developed. For example, if the amount of acetone which originates from the human bodies in some area is higher than the nationwide average, the local traditional food in the area may be high calorie food and, thus, there may be many people who are overweight or obese in the area. In such a case, the plan to reduce their intake of high calorie foods can be developed. In addition, to quantitatively monitor the effect of the plan, the attached substance detecting method according to the present exemplary embodiment can be used as a significantly effective tool.

As described above, the laundry washing machine according to the present exemplary embodiment can appropriately display, on a display unit, the result of detection performed by the detection unit and present the result of detection to the user.

In addition, the laundry washing machine displays the temporal variation of the result of detection of the predetermined substance for a specified person. Thus, the user can find out the information regarding the specified person in more detail. Note that the specified person may be the user themselves or a person other than the user.

Furthermore, the laundry washing machine can present a change in the physical condition of the specified person on the basis of the temporal variation of the result of detection for the person and display alert information if, for example, the physical condition is getting worse. The user can take an action plan to improve their health, such as a food plan and an exercise plan.

Fourth Exemplary Embodiment

The techniques described in all the above-described exemplary embodiments can be achieved in a cloud service of, for example, the following types. However, the types of cloud service in which the techniques described in all the above-described exemplary embodiments are applied are not limited thereto.

Service Type 1: Company-Owned Data Center Type

Figure 15:
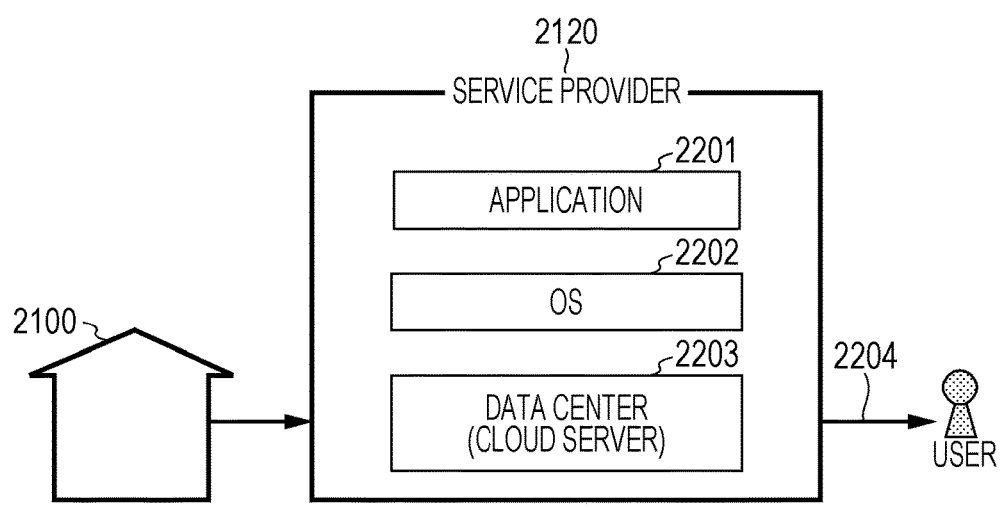
FIG. 15 illustrates a cloud service of Type 1 (a company-owned data center type)

FIG. 15 illustrates an example of a cloud service of Type 1 (a company-owned data center type). In the cloud service of this type, the service provider 2120 acquires information from a group 2100 and provides a service to users. In the cloud service of this type, the service provider 2120 has the function of the data center operating company. That is, the service provider owns the cloud server 2111 that manages big data. Accordingly, there is no data center operating company.

In the cloud service of this type, the service provider 2120 operates and manages a data center 2203 (the cloud server 2111). In addition, the service provider 2120 manages an operating system (OS) 2202 and an application 2201. The service provider 2120 provides a service 2204 using the OS 2202 and the application 2201 managed by the service provider 2120.

Service Type 2: IaaS Use Type

Figure 16:
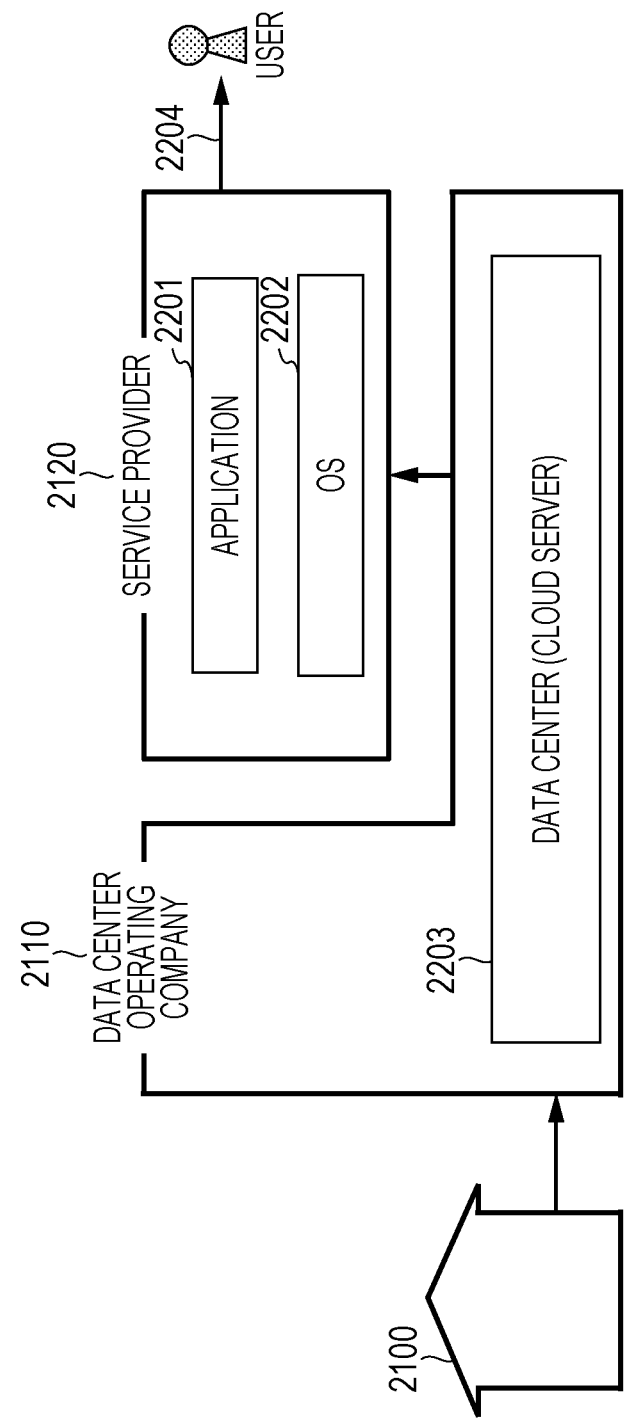
FIG. 16 illustrates a cloud service of Type 2 (an IaaS use type)

FIG. 16 illustrates an example of a cloud service of Type 2 (an IaaS use type). "IaaS" stands for an "infrastructure as a service". IaaS is a cloud service providing model that provides, as a service, the infrastructure itself for constructing and operating a computer system via the Internet.

In the cloud service of this type, the data center operating company 2110 operates and manages a data center 2203 (the cloud server 2111). In addition, the service provider 2120 manages the OS 2202 and the application 2201. The service provider 2120 provides a service 2204 using the OS 2202 and the application 2201 managed by the service provider 2120.

Service Type 3: PaaS Use Type

Figure 17:
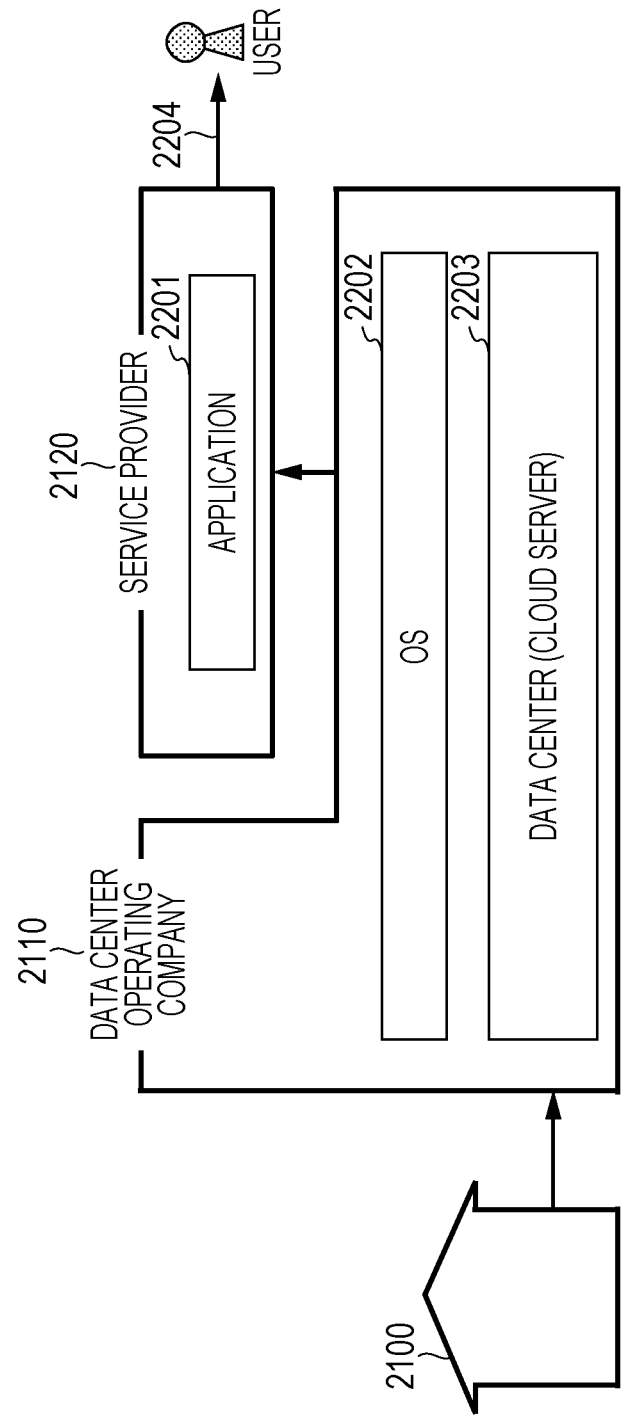
FIG. 17 illustrates a cloud service of Type 3 (a PaaS use type)

FIG. 17 illustrates an example of a cloud service of Type 3 (a PaaS use type). "PaaS" stands for a "platform as a service". PaaS is a cloud service providing model that provides, as a service, the platform serving as the base on which software is developed and executed via the Internet.

In the cloud service of this type, the data center operating company 2110 manages the OS 2202 and operates and manages the data center 2203 (the cloud server 2111). In addition, the service provider 2120 manages the application 2201. The service provider 2120 provides a service 2204 using the OS 2202 managed by the data center operating company 2110 and the application 2201 managed by the service provider 2120.

Service Type 4: SaaS Use Type

Figure 18:
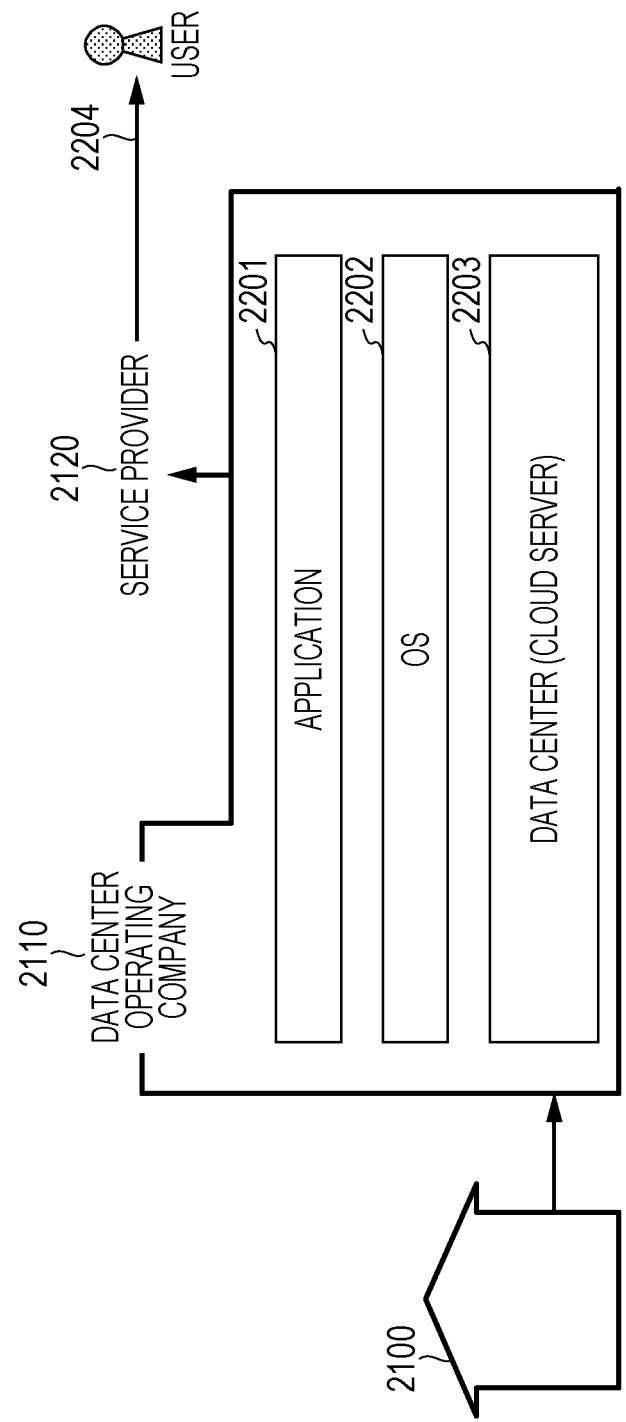
FIG. 18 illustrates a cloud service of Type 4 (an SaaS use type)

FIG. 18 illustrates an example of a cloud service of Type 4 (an SaaS use type). "SaaS" stands for a "software as a service". SaaS is a cloud service providing model that allows a company or an individual person (a user) that does not own a data center (a cloud server) to use, for example, an application provided by a platform provider that owns a data center (a cloud server) via a network, such as the Internet.

In the cloud service of this type, the data center operating company 2110 manages the application 2201 and the OS 2202 and operates and manages the data center 2203 (the cloud server 2111). In addition, the service provider 2120 provides a service 2204 using the OS 2202 and the application 2201 managed by the data center operating company 2110.

In any one of the above-described types, the service provider 2120 provides a service. In addition, for example, the service provider 2120 or the data center operating company 2110 may develop the OS, the application, or the database of big data by itself or ask a third party to develop the OS, the application, or the database of big data.

It should be noted that in any one of the above-described exemplary embodiments, the constituent elements may be configured from dedicated hardware or by executing a software program suitable for each of the constituent elements. The constituent elements may be realized by a program execution unit, such as a central processing unit (CPU) or a processor, that reads out a software program stored in a recording medium, such as a hard disk or a semiconductor memory, and executes the software program. The software that provides the laundry washing machine and the attached substance detecting method of each of the above-described exemplary embodiments is the following program.

That is, the program causes a computer to perform an attached substance detecting method for use in an attached substance detection system including the laundry washing machine that washes the laundry and that includes a wash tub allowing the laundry and water to be loaded thereinto. The attached substance detecting method includes separating some of the water in the wash tub and holding the some of the water, where the water contains a substance that was attached to the laundry and that is dissolved therein, detecting a predetermined substance contained in the held some of the water and outputting information indicating the result of detection, and dispensing a laundry detergent into the wash tub or instructing a user to add the laundry detergent to the wash tub after the some of the water is separated.

While the laundry washing machine of one or a plurality of aspects have been described with reference to the exemplary embodiments, the present disclosure is not limited to the exemplary embodiments. A variety of modifications of the present embodiment that are conceivable by those skilled in the art and an embodiment configured by combining constituent elements of different embodiments may be encompassed in the scope of one or a plurality of aspects of the present disclosure without departing from the spirit and scope of the present disclosure.

The present disclosure further increases the usefulness of a laundry washing machine and laundry services. In addition, the present disclosure provides a beneficial effect on the medical and insurance industries and improves the health of the user.

What is claimed is:

1. A laundry washing machine, comprising:
a wash tub;
a motor;
a holding unit, including a tank;
a detector;
a laundry detergent dispenser; and
a control unit, including a processor, configured to control the wash tub, the motor, the holding unit, the detector, and the laundry detergent dispenser,
wherein the control unit is configured to control the motor so that (i) after laundry is put into the wash tub and after water is dispensed into the wash tub, the motor works to agitate the laundry and the water in the wash tub, and (ii) stops before a laundry detergent is dispensed into in the wash tub;
wherein the control unit is configured to control the motor and the holding unit so that (i) after the motor works and before the laundry detergent is dispensed into in the wash tub, the holding unit separates a predetermined amount of the water in the wash tub, and (ii) holds the predetermined amount of the water in the tank, wherein the predetermined amount of water is less than an entire amount of the water which is dispensed into the wash tub;

wherein the control unit is configured to control the detector to detect a predetermined substance contained in the predetermined amount of the water held by the holding unit and output information indicating a result of detection, wherein the predetermined substance is a substance that is attached to the laundry before the laundry is put into the wash tub and that is dissolved in or mixed with the water dispensed into the wash tub after the laundry is put into the wash tub and before the predetermined amount of the water is separated by the holding unit and that is different from the laundry detergent; and wherein the control unit is configured to control the laundry detergent dispenser to dispense the laundry detergent into the wash tub or instruct a user to add the laundry detergent to the wash tub after the some of the water is separated.

2. The laundry washing machine according to claim 1, wherein the control unit is configured to control the wash tub to wash the laundry using the laundry detergent after the laundry detergent is dispensed by the laundry detergent dispenser or the laundry detergent is added by the user on the basis of the instruction from the laundry detergent dispenser, and wherein the control unit is configured to control the detector to perform the detection while the wash tub is in a wash cycle.

3. The laundry washing machine according to claim 1, wherein the control unit is configured to control the holding unit to separate the predetermined amount of the water in the wash tub after the laundry and the water are agitated in the wash tub by the motor driving and before the laundry detergent is dispensed into the wash tub.

4. The laundry washing machine according to claim 3, wherein the control unit is configured to control driving of the motor to agitate the laundry and the water in the wash tub after laundry is put into the wash tub and after water is dispensed into the wash tub, wherein the control unit is configured to control stopping the motor, wherein after the motor stops, the control unit is configured to control the holding unit to separate the predetermined amount of the water, wherein after the holding unit completes separating the predetermined amount of the water in the wash tub, the control unit is configured to control driving the motor again to agitate the laundry and the water again, and wherein the control unit is configured to control the laundry detergent dispenser to dispense the laundry detergent into the wash tub or to instruct the user to add the laundry detergent to the wash tub.

5. The laundry washing machine according to claim 4, wherein after the detector performs the detection, the control unit is further configured to control a wash course of the wash done by the laundry washing machine on the basis of the detection.

6. The laundry washing machine according to claim 5, wherein the wash course is defined as setting at least one of an amount of the laundry detergent dispensed by the laundry detergent dispenser, a time length of the wash cycle of the wash tub, and a time length of a rinse cycle of the wash tub and washing the laundry using the wash tub.

7. The laundry washing machine according to claim 4, further comprising:

an information aggregator that aggregates information on the basis of the result of detection output from the detector; and a display that displays the aggregated information, wherein after the detector performs the detection, the control unit is further configured to control the information aggregator to aggregate the information and to control the display to display the information aggregated by the information aggregator.

8. The laundry washing machine according to claim 4, further comprising:

a transceiver that communicates information with an external apparatus that aggregates information on the basis of the result of detection; and a display that displays information received from the external apparatus, wherein after the detector performs the detection, the control unit is further configured to control the transceiver to send, to the external apparatus, the result of detection and appliance identification information for identifying the laundry washing machine, and wherein when the transceiver receives, from the external apparatus, information aggregated on the basis of the result of detection, the control unit is further configured to control the display to display, on the display, the received aggregated information.

9. The laundry washing machine according to claim 4, further comprising:

a transceiver that communicates information with an external apparatus that aggregates information on the basis of the result of detection; and an individual identifier that identifies personal information regarding the laundry loaded into the wash tub, wherein after the detector performs the detection, the control unit is further configured to control the transceiver to send, to the external apparatus, the personal information, the result of detection, and appliance identification information for identifying the laundry washing machine, and wherein the control unit is further configured to control the external apparatus to send, to an external display terminal associated with the personal information, information aggregated on the basis of the result of detection.

10. The laundry washing machine according to claim 1, wherein the detector performs the detection every time the wash is done and outputs a plurality of results of the detection, and wherein the laundry washing machine further comprising an information accumulator that accumulates, in a writable recording medium, the result of detection in association with a time at which the result of detection is output every time the detector outputs the information; and a display that displays each of the results of detection accumulated in the recording medium in association with the time at which the result of detection was output.

11. The laundry washing machine according to claim 10, further comprising:

an individual identifier that identifies a person who wore the laundry, wherein the information accumulator further accumulates, in the recording medium, the result of detection in association with a personal ID indicating the person identified by the individual identifier, and wherein the display receives a specified personal ID representing a personal ID specified by the user, reads out, from the recording medium, the result of detection associated with the specified personal ID received, and displays each of the readout results of detection in association with the time at which the result of detection was output.

12. The laundry washing machine according to claim 11, wherein the display further displays information in accordance with a variation of a physical condition of the person, and the variation of the physical condition is estimated on the basis of a temporal variation of the amount of the substance detected by the detector.

13. The laundry washing machine according to claim 1, wherein the predetermined substance is a substance that had previously floated in the air and that is attached to the laundry before the laundry is put into the wash tub and that is dissolved in or mixed with the water dispensed into the wash tub after the laundry is put into the wash tub and before the predetermined amount of the water is separated by the holding unit and that is different from the laundry detergent.

14. The laundry washing machine according to claim 1, wherein the detector detects, as the predetermined substance, an antigen present in pollen.

15. The laundry washing machine according to claim 1, wherein the detector detects, as the predetermined substance, a substance that originates from a human body which wore the laundry and that is attached to the laundry.

16. The laundry washing machine according to claim 1, wherein the detector performs the detection using liquid chromatography.

17. The laundry washing machine according to claim 1, further comprising:

a window disposed in part of a housing of the laundry washing machine, wherein a component that constitutes the detector and that requires replacement is replaced with a new one through the window.

18. The laundry washing machine according to claim 1, wherein the holder includes a tank that holds the some of the water, a water channel that draws the some of the water in the wash tub into the tank, and a valve disposed in the water channel, and wherein the some of the water in the wash tub is held in the tank by opening the valve, and the some of the water is separated from the wash tub by closing the valve.

* * * * *